US010648019B2

(12) United States Patent
Joe et al.

(10) Patent No.: US 10,648,019 B2
(45) Date of Patent: May 12, 2020

(54) METHOD FOR THE DETECTION OF MULTIPLE TARGET NUCLEIC ACIDS USING CLAMPING PROBES AND DETECTION PROBES

(71) Applicant: PANAGENE INC., Daejeon (KR)

(72) Inventors: Goon Ho Joe, Daejeon (KR); Yong Tae Kim, Sejong (KR); Sung Kee Kim, Daejeon (KR); Jin Woo Kim, Daejeon (KR); Jae Jin Choi, Daejeon (KR); In Seong Wo, Daejeon (KR); Ji Hye Yoon, Gyeonggi-do (KR); Su Nam Kim, Daejeon (KR); Jun Ho Park, Daejeon (KR)

(73) Assignee: PANAGENE INC., Daejeon (KR)

( * ) Notice: Subject to any disclaimer, the term of this patent is extended or adjusted under 35 U.S.C. 154(b) by 94 days.

(21) Appl. No.: 14/648,909

(22) PCT Filed: Oct. 14, 2014

(86) PCT No.: PCT/KR2014/009611
§ 371 (c)(1),
(2) Date: Jun. 1, 2015

(87) PCT Pub. No.: WO2015/068957
PCT Pub. Date: May 14, 2015

(65) Prior Publication Data
US 2017/0198340 A1 Jul. 13, 2017

(30) Foreign Application Priority Data

Nov. 11, 2013 (KR) .................. 10-2013-0136429
Jun. 3, 2014 (KR) .................. 10-2014-0067582

(51) Int. Cl.
| C12Q 1/68 | (2018.01) |
| C07H 21/00 | (2006.01) |
| C12Q 1/6827 | (2018.01) |
| C12Q 1/6858 | (2018.01) |
| C12Q 1/6818 | (2018.01) |
| C12Q 1/6832 | (2018.01) |
| C12Q 1/686 | (2018.01) |
| C12Q 1/6886 | (2018.01) |

(52) U.S. Cl.
CPC ........... *C12Q 1/6827* (2013.01); *C12Q 1/686* (2013.01); *C12Q 1/6818* (2013.01); *C12Q 1/6832* (2013.01); *C12Q 1/6858* (2013.01); *C12Q 1/6886* (2013.01); *C12Q 2600/156* (2013.01)

(58) Field of Classification Search
CPC .................................. C12Q 1/68; C07H 21/00
See application file for complete search history.

(56) References Cited

U.S. PATENT DOCUMENTS

| 5,629,147 A * | 5/1997 | Asgari | C12Q 1/6804 435/5 |
| 5,714,331 A * | 2/1998 | Buchardt | C07H 21/00 435/6.14 |
| 7,803,543 B2 | 9/2010 | Chiou | |
| 8,815,515 B1 * | 8/2014 | Zhou | C12Q 1/686 435/6.1 |
| 2004/0009515 A1 * | 1/2004 | Liu | C12Q 1/6827 435/6.11 |
| 2008/0096766 A1 * | 4/2008 | Lee | C12Q 1/6851 506/6 |
| 2009/0291448 A1 * | 11/2009 | Jurisica | C12Q 1/6886 435/6.12 |
| 2010/0009355 A1 * | 1/2010 | Kolodney | C12Q 1/6858 435/6.18 |
| 2010/0297630 A1 * | 11/2010 | Reijans | C12Q 1/6818 435/6.1 |
| 2013/0005589 A1 * | 1/2013 | Matsumoto | C12Q 1/6858 506/7 |
| 2014/0087375 A1 * | 3/2014 | Kelley | C12Q 1/6816 435/6.11 |
| 2015/0176065 A1 * | 6/2015 | Powell | C12Q 1/6858 435/6.11 |
| 2016/0298177 A1 * | 10/2016 | Kelley | C12Q 1/6816 |

FOREIGN PATENT DOCUMENTS

| JP | 2000-503671 | 3/2000 |
| JP | 2006288353 A | 10/2006 |
| KR | 20110086963 A | 8/2011 |
| WO | 2013026027 A1 | 2/2013 |

OTHER PUBLICATIONS

Ahen, H. The Scientist 9(15) :20 (1995).*
Dominguez et al., Wild-type blocking polymerase chain reaction for detection of single nucleotide minority mutations from clinical specimens. Oncogene 24 : 6830 (2005).*
Englund et al. g-Substituted Peptide Nucleic Acids Constructed from L-lysine are a Versatile Scaffold for Multifunctional Display. Angew. Chem.Intl. Ed.46:1414(2007).*
Mauger et al.High-Specificity Single-Tube Multiplex Genotyping Using Ribo-PAP PCR, Tag Primers, Alkali Cleavage of RNA/DNAChimeras and MALDI-TOF MS. Human Mutation 34(1) : 266(2013—published online on Sep. 18, 2012).*
Mhlanga et al., Using Molecular Beacons to Detect Single-Nucleotide Polymorphisms with Real-Time PCR. Methods 25:463 (2001).*

(Continued)

*Primary Examiner* — Ethan C Whisenant
(74) *Attorney, Agent, or Firm* — Arent Fox LLP

(57) ABSTRACT

Disclosed is a probe mixture for real-time detection of target nucleic acids comprising at least one detection probe and at least one clamping probe for inhibiting amplification of wild type genes or unwanted genes, a kit using the same and a method for real-time detection of target nucleic acids using the mixture and the kit.

24 Claims, 11 Drawing Sheets

Specification includes a Sequence Listing.

(56) References Cited

OTHER PUBLICATIONS

Nagai et al., Genetic Heterogeneity of the Epidermal Growth Factor Receptor in Non-Small Cell Lung Cancer Cell Lines Revealed by a Rapid and Sensitive Detection System, the Peptide Nucleic Acid-Locked Nucleic Acid PCR Clamp. Cancer Research 65(16) :7276 (2005).*
Oh et al.,Detection of Low-Level KRAS Mutations Using PNA-Mediated Asymmetric PCR Clamping and Melting Curve Analysis with Unlabeled Probes. J. of Molecular Diagnostics 12(4) : 418 (Jul. 2010).*
Orum et al., Single base pair mutation analysis by PNA directed PCR clamping. Nucleic Acids Research 21 (23) : 5332(1993).*
Bernard et al., Homogeneous Multiplex Genotyping of Hemochromatosis Mutations with Fluorescent Hybridization Probes. Am. J. of Pathology 153(4) :1055(1998). (Year: 1998).*
Cy 5, PubChem Website (downloaded Nov. 4, 2017). (Year: 2017).*
Fluorescein, PubChem Website (downloaded Nov. 3, 2017). (Year: 2017).*
Luo et al.,Detection of rare mutant K-ras DNA in a single-tube reaction using peptide nucleic acid as both PCR clamp and sensor probe. Nucleic Acids Reseach 34 (2) : e12 (2006). (Year: 2006).*
Nazarenko et al. A closed tube format for amplification and detection of DNA based on energy transfer. Nucleic Acids Research 25(12) : 2516 (1997). (Year: 1997).*
Ortiz et al., PNA molecular beacons for rapid detection of PCR amplicons. Molecular and Cellular Probes 12 : 219 (1998). (Year: 1998).*
EP Extended Search Report and Search Opinion dated Jun. 17, 2016, regarding EP14860780.
Oerum H et al: "Single Base Pair Mutation Analysis by PNA Directed PCR Clamping", Nucleic Acids Research, Information Retrieval Ltd, GB, vol. 21, No. 23, Oct. 25, 1993 (Oct. 25, 1993), pp. 5332-5336, XP002006092, ISSN: 0305-1048 *the whole document*.
Shantanu Karkare et al: "Promising nucleic acid analogs and mimics: characteristic features and applications of PNA, LNA, and morpholino", Applied Microbiology and Biotechnology, Springer, Berlin, DE, vol. 71, No. 5, May 9, 2006 (May 9, 2006), pp. 575-586, XP019422061, ISSN: 1432-0614, DOI: 10.1007/S00253-006-0434-2 , *the whole document*.
Miyake et al: "Sensitive detection of FGFR3 mutations in bladder cancer and urine sediments by peptide nucleic acid-mediated real-time PCR clamping", Biochemical and Biophysical Research Communications, Academic Press Inc., Orlando, FL, US, vol. 362, No. 4, Sep. 5, 2007 (Sep. 15, 2007), pp. 865-871, XP022249522, ISSN: 0006-291X, DOI: 10.1016/J.BBRC.2007.08.092 *abstract 1; figure 1*.
Ji Eun Oh, et al.: "Detection of Low-Level KRAS Mutations Using PNA-Mediated Asymmetric PCR Clamping and Melting Curve Analysis with Unlabeled Probes," Journal of Molecular Diagnotics, Jul. 2010, vol. 12, No. 4, pp. 418-424.
Ying Hu, et al.: "Detection of K-ras Mutations in Azoxymethane-Induced Aberrant Crypt Foci in Mice Using LNA-Mediated Real-Time PCR Clamping and Mutant-Specific Probes," Mutation Research, 2009 vol. 677, pp. 27-32.
Japanese Office Action dated Mar. 22, 2017, regarding JP Application No. JP20160530173.
1st Notice of Grounds for Rejection dated Jun. 16, 2016, regarding Korean Application No. KR10-2014-0067582, and English translation.
Second Notice of Grounds for Rejection dated Mar. 28, 2017, regarding Korean Application No. KR10-2014-0067582, and English translation.
First Office Action dated Feb. 1, 2018, regarding Chinese Application No. 201480061608.3.
Second Office Action dated Oct. 17, 2018, regarding Chinese Application No. 201480061608.3.
First Office Action dated Sep. 28, 2018, regarding Japanese Application No. JP2017-199346.
Ethan A. Englund and Daniel H. Appella: "Y-Substituted Peptide Nucleic Acids Constructed From L-Lysine are a Versatile Scaffold for Multifunctional Display", Angew. Chem. Int. Ed., 2007, vol. 46, p. 1414-1418.
Zhang Bingbo, et al.: "Systemic Comparison between PNA Probe and DNA Probe", Acta Polyrnerica Siniica, Sep. 2006.
Communication from European Patent Office (and Annex) dated Dec. 14, 2018, regarding EP Application No. EP14860780.7.
Examination Report dated Mar. 18, 2019, regarding India Application No. 201627020008.

* cited by examiner

[Fig. 1]
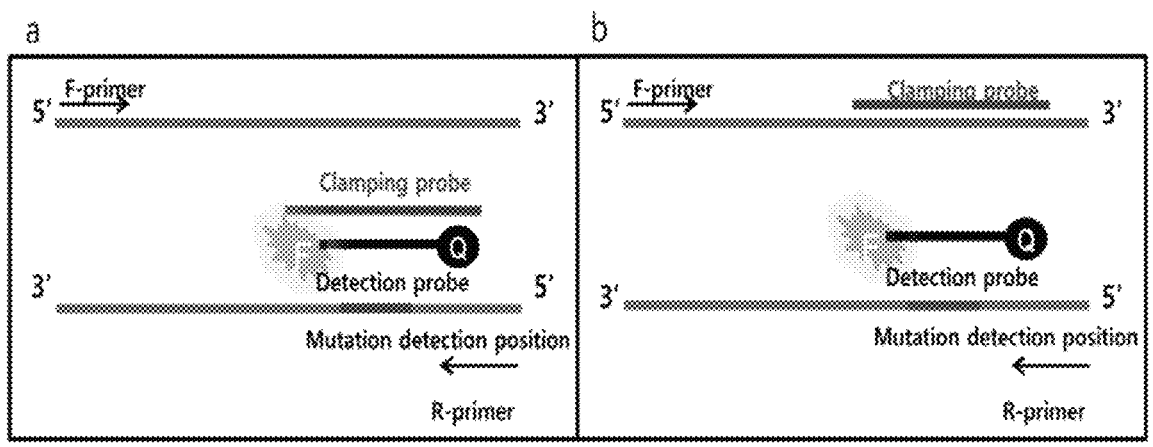
[Fig. 2]
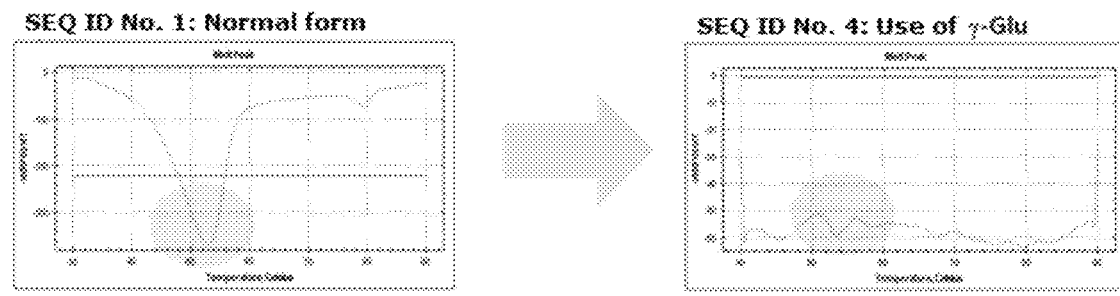
[Fig. 3]
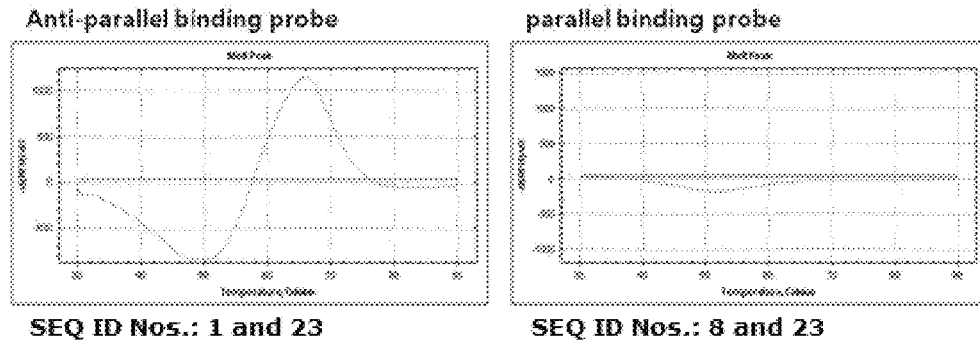

[Fig. 13a]
(A) Examples of G12D-perfect match, G12A,V,S Mismatch, Wild clamping
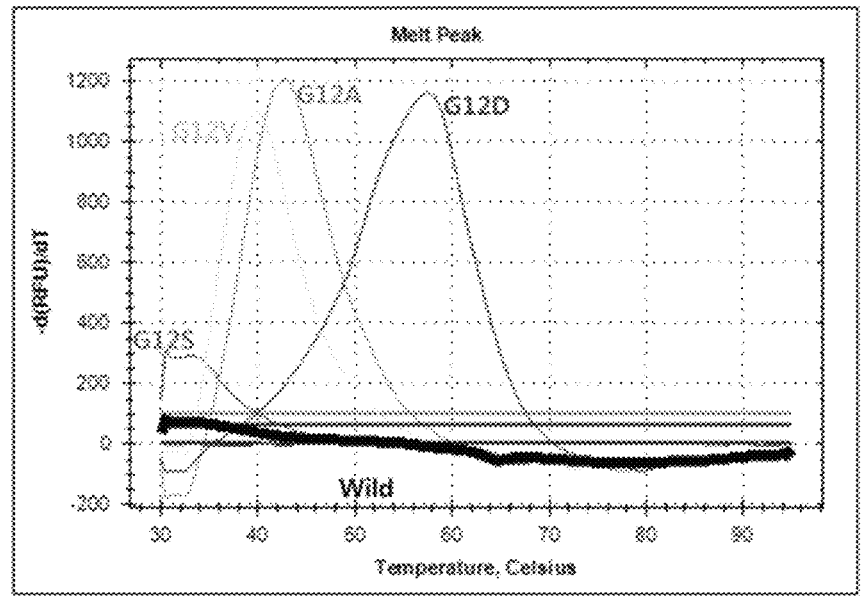
[Fig. 13b]
(B) Examples of G12V-perfect match, G12D,A,S-Mismatch, wild-clamping
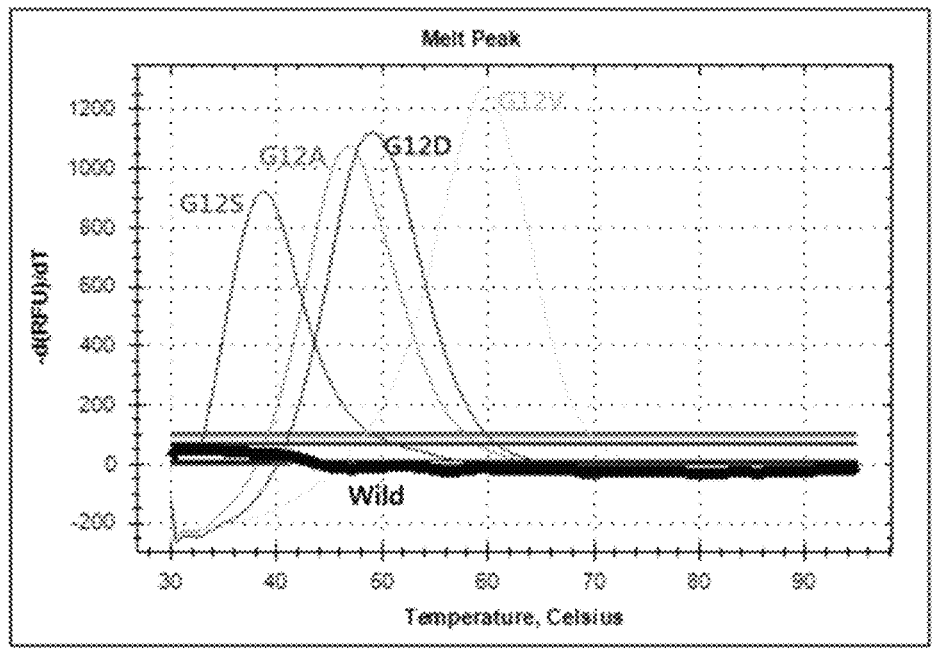

[Fig. 14a]
(A) Wild : Mutant = 100(25ng) : 1(250pg) _ 1%
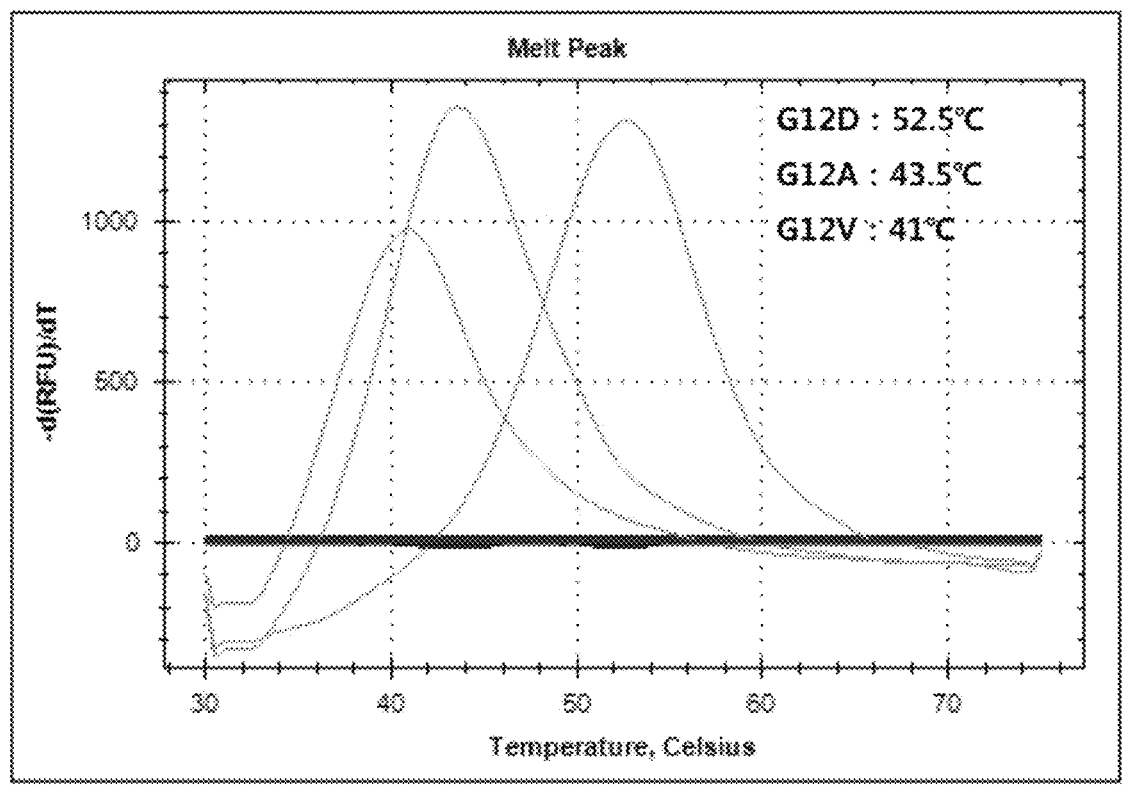

[Fig. 14b]
(B) Wild : Mutant = 100(25ng) : 0.1(25pg) _ 0.1%
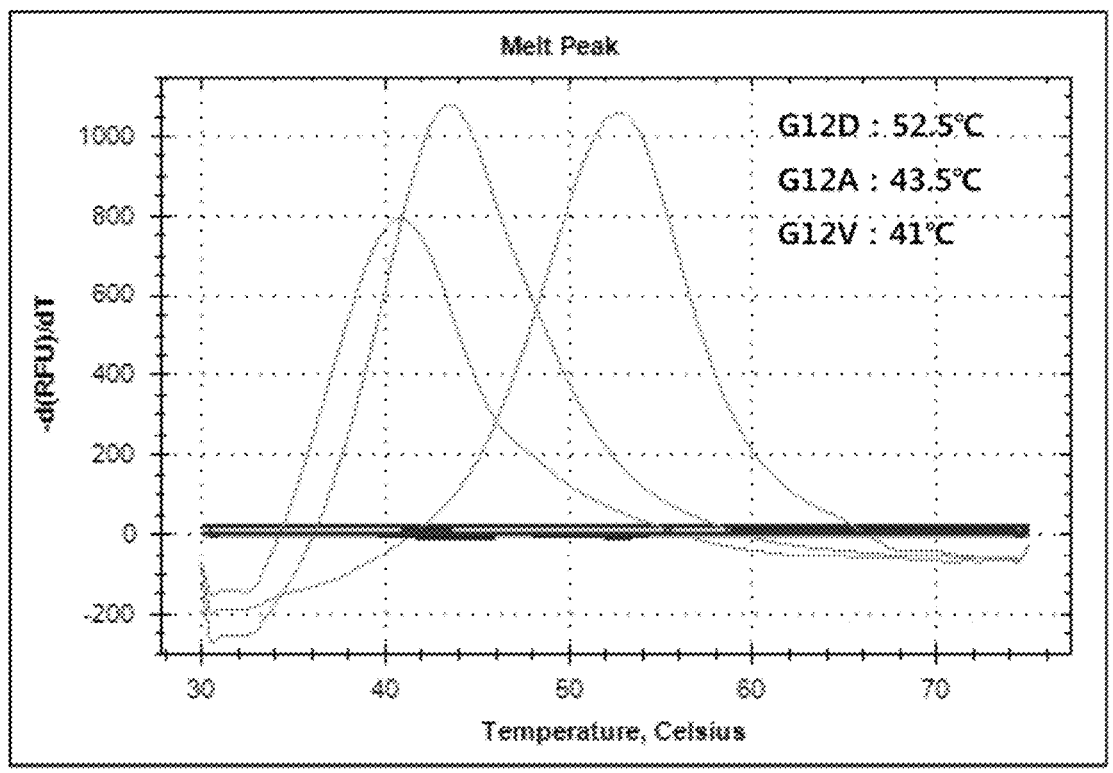

[Fig. 14c]
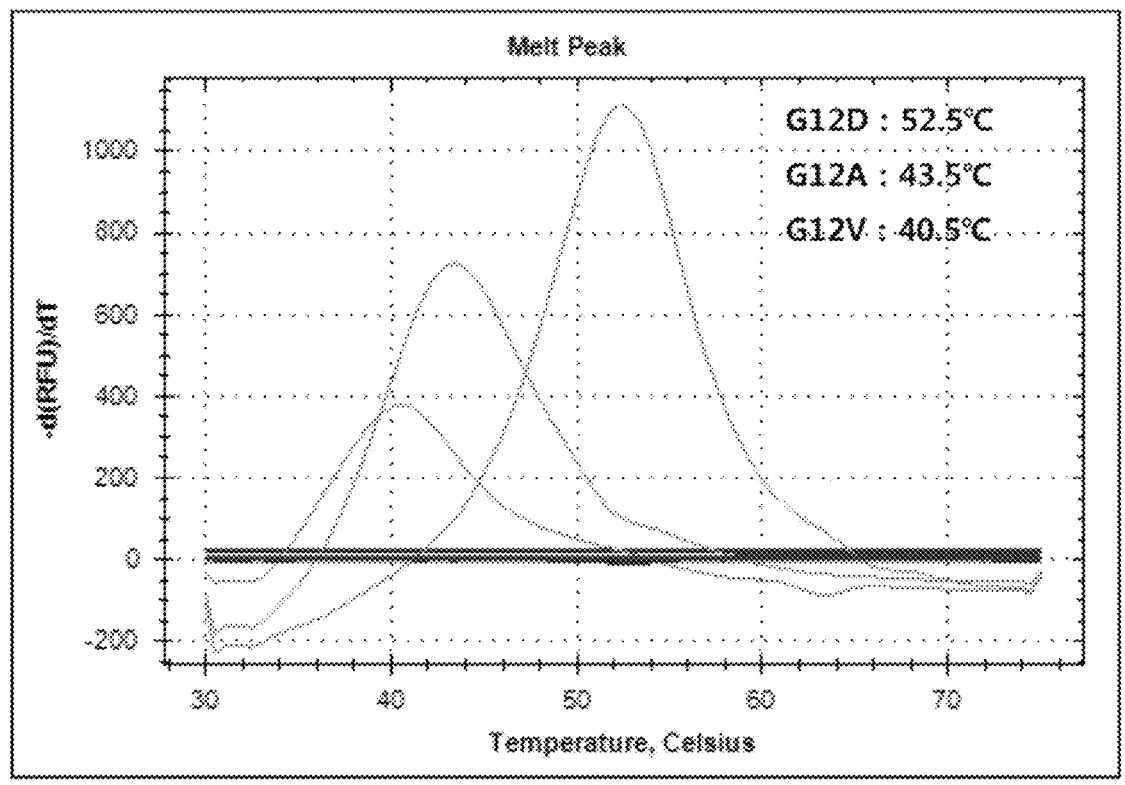

[Fig. 14d]
(D) Wild : Mutant = 100(25ng) : 0 _ 0%
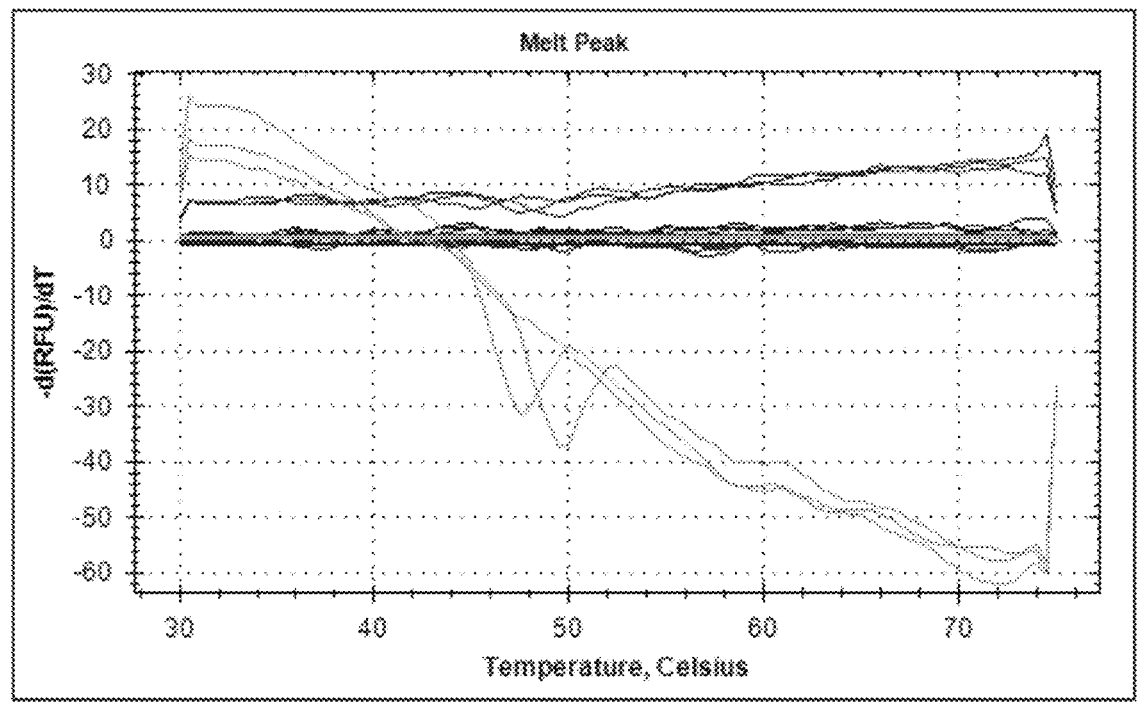

[Fig. 15a]
(A) Analysis of melting temperature of DNA target of SEQ ID No. 37
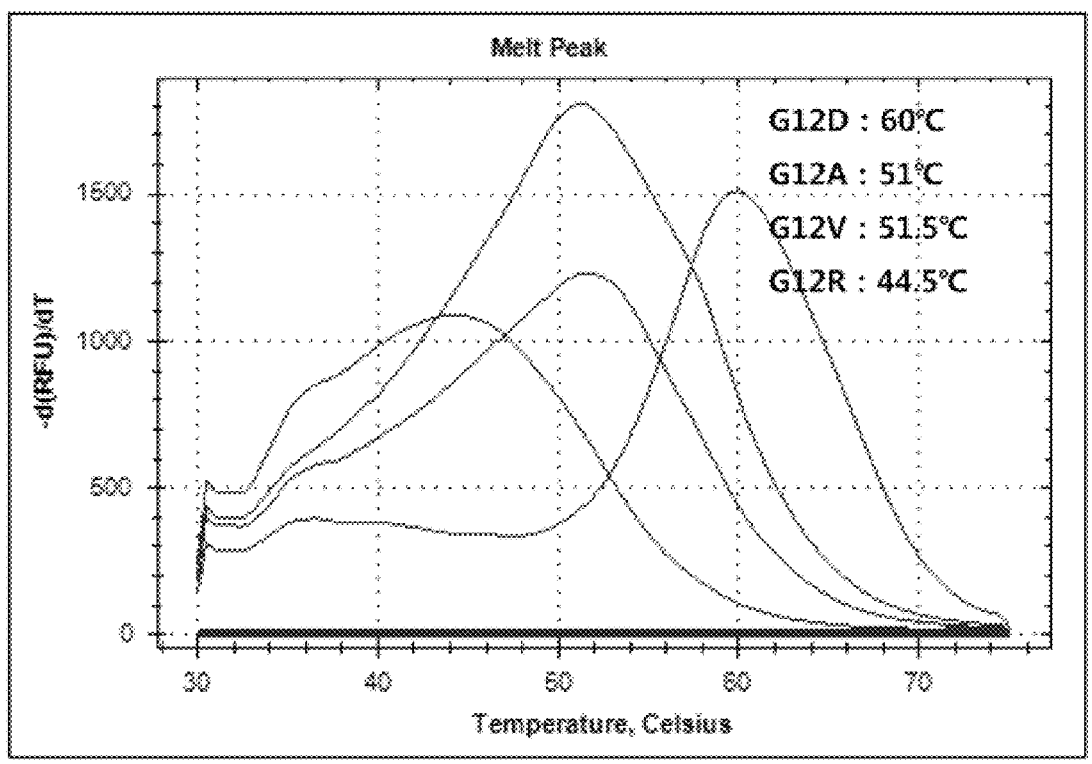

[Fig. 15b]
(B) Analysis of melting temperature of DNA target of SEQ ID No. 38
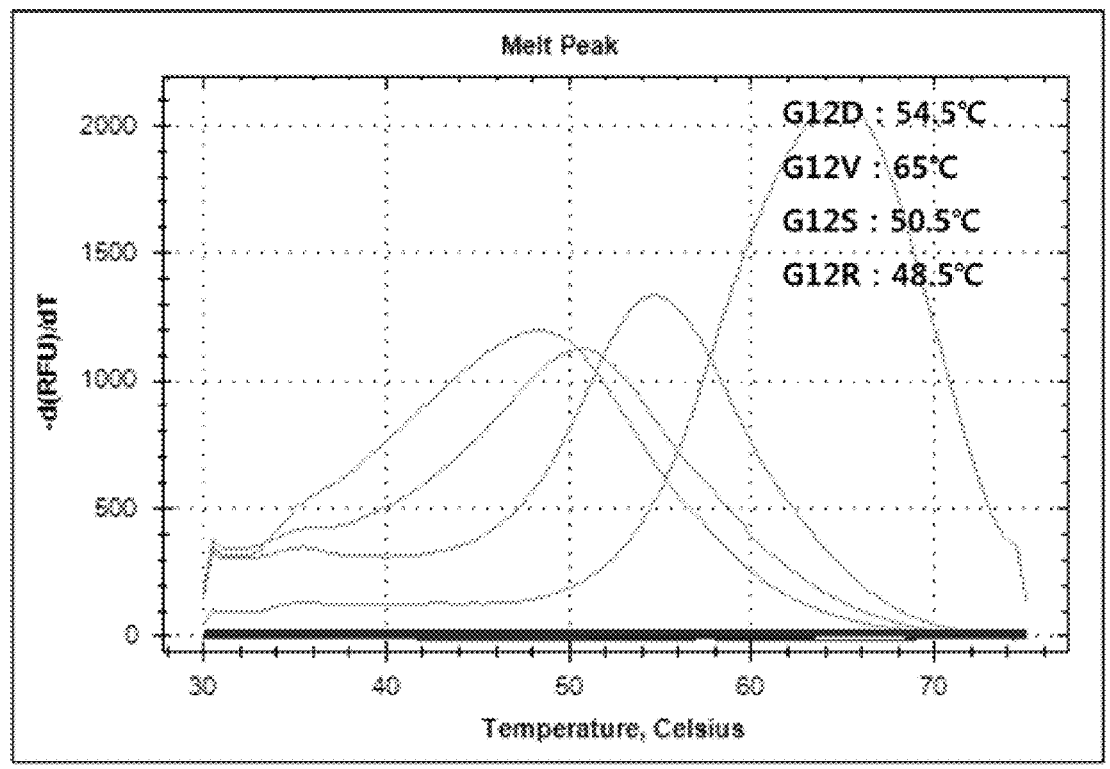

METHOD FOR THE DETECTION OF MULTIPLE TARGET NUCLEIC ACIDS USING CLAMPING PROBES AND DETECTION PROBES

CROSS-REFERENCE TO RELATED APPLICATIONS

This application is a PCT application of PCT/KR2014/009611 filed on Oct. 14, 2014, entitled "METHOD FOR THE DETECTION OF MULTIPLE TARGET NUCLEIC ACIDS USING CLAMPING PROBES AND DETECTION PROBES, which is based on KR 10-2014-0067582 filed on Jun. 3, 2014, which is based on KR10-2013-0136329 filed on Nov. 11, 2013, all of which are hereby expressly incorporated by reference in their entireties.

TECHNICAL FIELD

The present invention relates to a method for the detection of target nucleic acids using clamping probes and detection probes. More specifically, the present invention relates to a method for simultaneous detection of multiple target nucleic acid using a probe mixture for real-time detection of target nucleic acids comprising at least one detection probe and at least one clamping probe for inhibiting amplification of wild type genes or unwanted genes, and a kit using the same.

BACKGROUND ART

A gene is a very important substance which expresses the traits of a living organism through transcription and translation and conveys the traits to its offspring. It is composed of a base sequence having A (adenine), C (cytosine), G (guanine) and T (thymine) as their base units. The base sequence of a gene determines the traits of a living organism. Analysis of the base sequence and nucleotide polymorphism of genes is very important in conducting researches on biological information. For example, nucleotide polymorphism analysis makes it possible to diagnose heredity related diseases and prescribe personalized medicine according to genetic traits. Also, the analysis allows to diagnose infection viruses and distinguish drug resistant bacteria. In addition, the analysis can be broadly applied to various fields such as species distinction of living organism and forensic medicine, etc.

Particularly, in the field of treatment of cancer, which has been the number one cause of death in Korea since 1983, various researches on genomic abnormalities have been underway since it was found that genomic abnormalities such as mutations of oncogenes, mutations or deregulations of tumour suppressor genes, and chromosomal abnormalities, etc. are directly involved in the occurrence of cancer and prognosis determination of drugs (Fearson E R et al., *Cell.*, 1990, 61:759; K. W Kinzler et al., *Cell.*, 1996, 87:159; Manuel Serrano et al., *Cell.*, 1997, 88:593; Amado R G et al., *J. Clin. Oncol.*, 2008, 26:1626; Raponi M et al., *Curr Opin. Pharmacol.*, 2008, 8:413; Siena S et al., *J. Natl. Cancer Inst.*, 2009, 101:1308).

For this reason, detection of mutations with clinical significance is very important, and accordingly a wide variety of detection methods which vary depending on the analysis purpose or genotype are continuously being reported (Taylor C F, Taylor G R. *Methods Mol. Med.*, 92:9, 2004). Particularly, in somatic mutations, mutant genes exist at a very low frequency of about 0.1~100 bases per megabase of wild type genes depending on the type of tumour.

Also, the number of mutant cancer cells existing in analysis samples is considerably small compared to the number of normal cells, and thus it is very difficult to detect them and accordingly an advanced detection technique is required for the detection (Chung et al., *Clin Endocrinol.*, 65:660, 2006; Trovisco et al., *J Pathol.*, 202:247, 2004).

Representative methods for detecting a minute amount of mutation as in the above include various analysis methods based on real-time PCR technology, such as allele specific PCR method specifically amplifying mutants by using a mutant specific primer in order to selectively increase a small amount of mutant genes (Rhodes et al., *Diagn mol pathol.*, 6:49, 1997), scorpion real-time allele specific PCR method (DxS' scorpions and ARMS) (Mark et al., *Journal of Thoracic Oncology*, 4:1466, 2009), CAST PCR method detecting amplification products excluding the position where mutation occurred by using Taqman probe after inhibiting amplification of wild type genes and selectively amplifying only mutant genes by using allele specific primer technology and minor groove binder (MGB)-probe (Didelot A et al., *Exp Mol Pathol.*, 92:275, 2012), cold-PCR method increasing sensitivity of mutants by using critical denaturation temperature (Tc) (Zuo et al., *Modern Pathol.*, 22:1023, 2009), etc. Such technologies can be applied easily and quickly to various diagnoses, and are good technology for diagnosing and analyzing mutation of cancer related genes (Bernard et al., *Clinical Chemistry*, 48:1178, 2002).

However, in case of the above methods, it is difficult to design experiments for reasons such as that a primer amplifying only mutants should be designed, and the critical denaturation temperature should be precisely maintained, etc. Also, in the method using an allele specific primer, false positive results may be obtained if mispriming occurs. Also, Taqman and scorpions probe methods, currently most widely used, have problems that they are not capable of conducting simultaneous multiple analysis using melting curve analysis of a probe, and thus that the number of genes detectable in one tube depends on the number of fluorescences detectable by the real-time PCR apparatus.

Recently, various molecular diagnosis technologies have been developed for detecting somatic mutation through real-time PCR technology. However, in the aspect of usefulness, they did not achieve a remarkable development, and it is necessary to develop a technology with high sensitivity and specificity which is capable of simultaneous multiple quantitative analysis in a short period of time.

Peptide nucleic acid (PNA) was reported in 1991 by Nielsen as a nucleic acid analogue having N-(2-aminoethyl) glycinamide as its backbone (Nielsen P E et al., *Science*, 254(5037):1497, 1991). The PNA backbone is electrically neutral, and thus has higher specificity and selectivity than DNA probe with respect to target nucleic acids having a complementary base sequence. Also, it is possible, by introducing a specific functional group at the alpha (α), gamma (γ) position or linker part of the backbone, to freely adjust physical properties of PNA, such as cell penetration and its melting temperature from the target nucleic acid (Englund E A et al., *Angew. Chem. Int. Ed. Engl.*, 46:1414, 2007; Stefano Sforza et al., *Eur J. Org. Chem.*, 16:2905, 2000; Roberto Corradini et al., *Curr Top. Med. Chem.*, 11:1535. 2011). Further, it has an advantage of not being decomposed by nuclease or protease, and thus is very useful in molecular diagnosis methods using a probe (Egholm et al., *Nature*, 365:556, 1993; Nielsen et al., *Bioconjugate Chem.*, 5:3, 1994; Demidov, et al., *Biochem. Pharmacol.*, 48:1310, 1994). Using these advantages of PNA, the PCR clamping technology was developed in 1993 (Henrik Orum et al.,

*Nucleic Acids Res.,* 21:5332, 1993). This technology inhibits PCR amplification of a gene that should not be amplified by binding a PNA probe to the gene. When a PNA probe complementary to a wild type gene is used, the amplification of the wild type gene is inhibited during PCR reaction, thus making it possible to quickly and accurately detect mutants, which are present in a minute amount when compared to the wild type gene.

Currently, various techniques using the PNA clamping technology are being reported. Hereinafter, the characteristics of methods for selectively amplifying genes by using the PNA clamping technique will be briefly described.

PNA-LNA clamp method (US Patent Publication No. 2013-0005589; Yoshiaki Nagai et al. *Cancer Res.,* 65(16): 7276, 2005) is a method for selective amplification and selective detection designed such that a PNA clamping probe having a wild-type gene sequence and an LNA taqman probe for detection having a mutant gene sequence competitively hybridize with the target site. However, this method uses the taqman probe method where a DNA polymerase having 5'→3' exonuclease activity degrades a mutation probe labeled with a fluorescent substance and a quencher to allow fluorescence. Thus, according to this method, the melting temperature (Tm) value of the probe cannot be analyzed, and it is not possible to detect multiple targets with one fluorescence.

PNA hyb probe (PNA as both PCR clamp and sensor probe; US Patent Publication No. 2008-0176226) is a technology designed to allow a PNA probe to conduct clamping and detecting simultaneously by changing the donor probe in Roche's conventional hyb probe system to a PNA probe. However, since the technology still has a limitation that it must comprise an anchor probe, it is difficult to design the probe, and the use of a long anchor probe disables simultaneous detection of multiple mutations at adjacent positions. Also, the use of one PNA probe conducting clamping and detecting simultaneously makes difficult an analysis in determination of multiple mutant genotypes within the same codon through the melting curve analysis of the PNA probe because the melting temperatures of the PNA from each of the mutant genotypes is not significantly different from one another.

PNA clamping and intercalator detection method (Makito Miyake et al., *Biochem Biophys Res Commun.,* 362:865, 2007) is a method of detecting amplification product by using an intercalator after selectively amplifying only mutant genes while clamping wild-type gene by using a PNA probe. It is not capable of conducting simultaneous multiple detection, and in case the wild-type gene is not completely clamped, false positive results may occur, and thus it is difficult to analyze the results.

The method of using PNA and unlabeled DNA probe (Ji Eun Oh et al., *J Mol Diagn.,* 12:418, 2010) is a method of analyzing the melting curves of an unlabeled DNA probe from a mutant gene by using an intercalator after clamping wild-type gene with a PNA probe. It has problems that it is not capable of specific real-time amplification curve analysis and simultaneous multiple detection and has low sensitivity.

DETAILED DESCRIPTION

Technical Subject to be Achieved

As a result of conducting researches to solve the above problems, the present inventors found that, by using a mixture of a clamping probe and a fluorescent detection probe comprising a fluorescent substance and a quencher simultaneously to selectively detect the desired genes with high sensitivity, it is possible to detect the target nucleic acid in real-time and easily detect adjacent mutations. Also, the inventors found that by increasing the difference in the melting temperature of probes between the wild-type gene and target nucleic acid gene, it is possible to detect and quantify multiple target nucleic acids simultaneously and determine the genotypes thereof through amplification curve and melting curve analysis. Thereby, the inventors completed the present invention.

Also, the inventors found that by using a probe mixture to detect the target nucleic acid in real-time comprising a detection probe and a clamping probe, each structurally modified by changing the three-dimensional structure or adding electric charge, etc., the binding energy of hetero dimer and self dimer is decreased and the specificity to single nucleotide variation is increased, which makes it easy to selectively amplify and detect a minute amount of target nucleic acid gene.

The probe mixture system of the present invention can be used in various molecular diagnosis technologies such as molecular diagnosis, prenatal diagnosis, early diagnosis, cancer diagnosis, genetic associated diagnosis, diagnosis of genetic character, diagnosis of infection virus, determination of drug resistant bacterium, forensic medicine, determination of species of living organism, etc.

Means for Achieving the Subject

In order to achieve the above purpose, the present invention provides a probe mixture for real-time detection of target nucleic acids comprising at least one detection probe and at least one clamping probe for inhibiting amplification of wild type genes or unwanted genes, a method for simultaneous detection of multiple target nucleic acids using the probe mixture, and a kit for diagnosing molecules using the method.

The probe mixture of the present invention provides a method for simultaneous detection of multiple target nucleic acids using a clamping probe and at least one detection probe to which a reporter and a quencher are attached, both of which are competitively hybridized with the same strand, or a method for simultaneous detection of multiple target nucleic acids using a clamping probe and at least one detection probe to which a reporter and a quencher are attached, which are hybridized with complementary strands.

Effect of the Invention

By using the method for detecting target nucleic acid according to the present invention, it is possible to inhibit amplification of wild type genes or unwanted genes. Also, through selective amplification and selective detection of a minute amount of target nucleic acid genes, the method allows to effectively detect single nucleotide variation and mutation caused by loss or insertion of base in a sample. Also, by using multiple detection probes and multiple amplification inhibition probes, the method enables to simultaneously analyze real-time amplification curve and melting curve, which allows to not only simultaneously detect and quantify multiple target nucleic acids but also determine genotype by melting curve analysis. Also, the method makes it possible to detect the target with high sensitivity, and thus can be very usefully used for early diagnosis requiring the detection of a trace of the target.

BRIEF DESCRIPTION OF DRAWINGS

FIG. 1 is a schematic diagram of a probe mixture. Drawing a in FIG. 1 is a schematic diagram of a probe mixture comprising a clamping probe and a detection probe competitively hybridizing on the same strand, and drawing b in FIG. 1 is a schematic diagram of a probe mixture comprising a clamping probe and a detection probe hybridizing on complementary strands.

FIG. 2 shows graphs illustrating the decrease in melting temperature of the self dimer of PNA probes imparted a three-dimensional structure.

FIG. 3 shows graphs illustrating the melting temperature of the hetero dimer of a PNA detection probe binding in anti parallel orientation to the clamping probe and a PNA detection probe binding in parallel orientation to the clamping probe.

FIG. 13 shows graphs illustrating the melting curves of a mutant gene in perfect match with the probe for detection, a mutant gene in mismatch with the probe for detection and a wild type gene. The sequence of the detection probe in FIG. 13(A) is SEQ ID No. 33, and the mutant gene in perfect match is G12D. The sequence of the detection probe in FIG. 13(B) is SEQ ID No. 34, and the mutant gene in perfect match is G12V.

FIG. 14 shows graphs illustrating the change of detection sensitivity according to the change in the mixing ratio of wild type gene and mutant gene. FIG. 14(A) is a graph illustrating the sensitivity of mutation detection of a sample containing 1% of mutant genes (G12D, G12A, G12V). FIG. 14(B) is a graph illustrating the sensitivity of mutation detection of a sample containing 0.1% of the mutant genes. FIG. 14(C) is a graph illustrating the sensitivity of mutation detection of a sample containing 0.01% of the mutant genes.

FIG. 15 shows graphs of melting curves using probes with no specific change in structure, which illustrate graphs of the melting curves of probes for detection and target DNAs. The sequence of the detection probe in FIG. 15(A) is SEQ ID No. 37, and the sequence of the detection probe in FIG. 15(B) is SEQ ID No. 38.

EMBODIMENTS FOR CARRYING OUT THE INVENTION

Unless defined otherwise, all technical and scientific terms used in the present specification have the same meanings as those generally understood by a person having ordinary skill in the art. The nomenclature used in the present specification is well known and generally used in the technical field.

The present invention relates to a method for simultaneous detection of multiple target nucleic acids using a clamping probe for inhibiting amplification of wild type genes or unwanted genes and a detection probe to which a reporter and a quencher are attached.

The term "detection probe" in the present invention means a probe that can selectively detect a target nucleic acid gene to be detected. The term "clamping probe" means a probe that can inhibit the elongation of polymerase between PCR reactions by complementarily binding to wild type genes or unwanted genes. The term "probe mixture" means a probe system comprising at least one detection probe and at lease one clamping probe.

The term "target nucleic acid" in the present invention means all types of nucleic acids to be detected, and may include or may not include a mutant gene. This can be characterized by all types of DNAs including genomic DNA, mitochondrial DNA, and viral DNA or all types of RNAs including mRNA, ribosomal RNA, non-coding RNA, tRNA, viral RNA, etc., but is not limited thereto. It is annealed or hybridized with a primer or a probe under hybridizing, annealing or amplifying conditions.

The term "hybridization" in the present invention means complementary single strand nucleic acids forming a double-strand nucleic acid. Hybridization occurs when two nucleic acid strands are in a perfect match. Hybridization may occur even when some mismatch bases exist. The degree of complementarity required for hybridization may vary depending on hybridization conditions such as temperature, in particular.

The term "mutation" in the present invention means a variation in the base sequence of wild type gene, including not only single nucleotide polymorphism (SNP) but also variation caused by substitution, loss or insertion of base. Also, mutation includes somatic mutation and germline mutation that may occur naturally, and also includes, without limitation, artificial mutation, etc. where the variation in the base sequence was artificially induced. The term "somatic mutation" in the present invention refers to a gene mutation occurring in somatic cells. Somatic mutation is known as the main cause of tumorigenesis by deregulation in signal transduction process, etc. Examples of significant "somatic mutation" include various cancer related genes such as KRAS, BRAF, EGFR, JAK2, HER2, BCL-ABL, NRAS, HRAS, IDH1, IDH2, C-KIT, TP53, EGFR, PIK3CA, etc. In the present invention, the inventors confirmed from the examples for mutations of the somatic gene K-ras (V-Ki-ras2 Kirsten rat sarcoma viral oncogene homolog), that the present invention works, and thus completed the invention.

Figure 12:
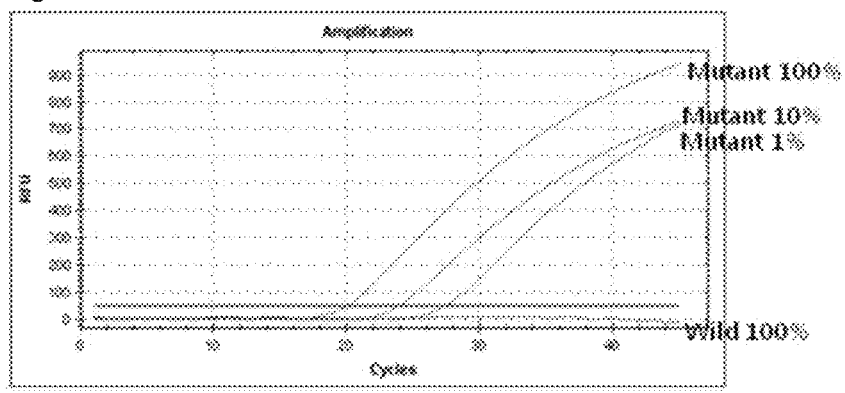
FIG. 12 shows a graph illustrating the amplification curve of T790M, which is an EGFR gene mutant, using an mgb-Taqman probe for detection-PNA probe for clamping.

In the present invention, the detection probe and clamping probe can be any nucleic acid or nucleic acid analogue complementarily binding to the target nucleic acid, selected from a group consisting of oligonucleotides, peptide nucleic acids (PNA) and locked nucleic acid (LNA). In general, polymerase for PCR has nuclease activity, which may lead to a damage to a probe. Thus, it is recommended to use synthetic nucleic acid such as PNA, which is stable to nuclease. Also, since the detection probe plays a role of selectively detecting the target nucleic acid gene, probes for the detection of nucleic acid which are well known in the pertinent art can be used. In order to confirm whether the target nucleic acid can be detected even when the detection probe of the present invention is a nucleic acid analogue other than PNA, an analysis was carried out using MGB-taqman as the detection probe. As a result, it was confirmed from real-time amplification curve analysis that the system of MGB-taqman probe for detecting mutation and the PNA probe for clamping wild type genes operate on different strands (FIG. 12).

In the present invention, preferably, a PNA probe is used. The PNA probe is an artificially synthesized DNA and can specifically bind to the target DNA or RNA. Also, since PNA probe is stable against nuclease, it allows a probe-based melting curve analysis. Also, PNA probe has a property of inhibiting the progress of polymerase after binding to DNA. Thus, in the present invention, the PNA probe designed to be completely hybridized with the wild type gene is used as a PNA clamping probe, and the PNA detection probe for simultaneous detection of multiple target nucleic acids is designed to be completely hybridized with the target nucleic acid gene.

Also, in accordance with the present invention, modification can be made to the three-dimensional structure of the clamping probe and detection probe by attaching a specific group such as the side chain of a natural amino acid or synthetic amino acid at the N-terminus, C terminus of the probe or the alpha, beta, gamma, linker position of the probe (synthetic nucleic acid) backbone. The amino acid may or may not have an electric charge, or may have a negative or positive charge, but is not limited thereto. Any method for changing the three-dimensional structure of probe or imparting electric charge which are known in the pertinent art can be used.

The detection probe in the present invention can have a reporter and a quencher capable of quenching reporter fluorescence attached at both terminals thereof, and can include an intercalating fluorescent substance.

The term "reporter" refers to a substance absorbing and emitting light of a specific wavelength to emit fluorescence, and which labels a probe to identify whether the target nucleic acid and the probe were hybridized. The reporter can be at least one selected from a group consisting of fluorescein, fluorescein chlorotriazinyl, rhodamine green, rhodamine red, tetramethylrhodamine, FITC, oregon green, Alexa Fluor, FAM, JOE, ROX, HEX, Texas Red, TET, TRITC, TAMRA, cyanine-based dye and thiadicarbocyanine dye.

Also, the term "quencher" means a substance absorbing the light generated by the reporter to reduce the strength of the fluorescence. The quencher can be at least one selected from a group consisting of Dabcyl, TAMRA, Eclipse, DDQ, QSY, Blackberry Quencher, Black Hole Quencher, Qxl, Iowa black FQ, Iowa black RQ, IRDye QC-1, but is not limited thereto. Quencher reduces the strength of fluorescence to a different extent depending on its type, and thus may be used in consideration of this matter.

In the present invention, multiple target nucleic acids are detected simultaneously by using a probe mixture for real-time detection of target nucleic acids comprising at least one detection probe and at least one clamping probe for inhibiting amplification of wild type genes or unwanted genes.

The method for simultaneous detection of multiple target nucleic acids using the probe mixture of the present invention is characterized by using one or at least one clamping probe inhibiting the elongation of polymerase by complementarily binding to wild type genes or unwanted genes to selectively amplify the target nucleic acid gene to be detected, and using one or at least one detection probe for specifically detecting the target nucleic acid to detect the presence or concentration of multiple target nucleic acids. Detection of the target nucleic acid using a probe mixture allows the simultaneous analysis of real-time amplification curve and melting curve.

As illustrated in FIG. 1, the clamping probe and detection probe of the present invention hybridize with the same strand of the target DNA (drawing a in FIG. 1), or the clamping probe and detection probe hybridize with complementary strands (drawing b in FIG. 1), thereby blocking wild type genes and detecting target nucleic acid genes simultaneously. That is, if the clamping probe is hybridized with a perfect match with the wild type gene, amplification of the wild type gene can be inhibited, which makes it possible to selectively amplify and detect a trace of the target nucleic acid gene. Also, it is possible to simultaneously detect multiple target nucleic acids, by using at least one detection probe.

The process of amplifying the target DNA using a probe mixture will be explained in more detail below. In the annealing step, each of the clamping probe and detection probe is annealed to the same strand or different complementary strands. The detection probe having a reporter and a quencher specifically binds to the target nucleic acid gene to be detected, thereby emitting an amplification curve signal (fluorescence). In the subsequent extension step, the clamping probe is still hybridized with the wild type gene or unwanted genes, and thus inhibits amplification of the wild type gene or unwanted genes. The detection probe is separated from the target nucleic acid to allow amplification to proceed, because it is designed to have a melting temperature lower than the temperature of the extension of the target nucleic acid.

The amplification process allows a real-time analysis of the amplification curve. Also, a melting curve analysis is possible by using the amplification product generated by the amplification process. In the melting curve analysis step, at low temperature, the detection probe is hybridized with the target nucleic acid gene, thereby emitting a fluorescence signal, but as the temperature rises, it is separated from the target nucleic acid and thus fluorescence is quenched.

Meanwhile, among the clamping probe and detection probe in the probe mixture of the present invention, those designed to operate from different directions of the target DNA chain are highly likely to form a hetero dimer. Thus, in order to reduce the hetero dimer binding energy of the clamping probe or detection probe, it is preferable to modify the detection probe or clamping probe structurally by changing its three-dimensional structure, imparting electric charge, etc. By this change, the binding energy of the hetero dimer or self dimer of probes was reduced, which made it easy to adjust the melting temperature of probes. Thereby, the detection system was completed.

In an embodiment of the present invention, in order to confirm the difference in melting temperature, PNA probes were synthesized by introducing the side chain of negatively charged L-glutamic acid or D-glutamic acid, uncharged L-alanine or D-alanine, or of positively charged L-lysine or D-lysine at the gamma position of PNA, and L-lysine or L-glutamic acid at the linker position (Table 1).

According to the results of the analysis of the characteristics of each modified PNA probe by using a melting curve analysis method, it was found that in the PNA probes of SEQ ID Nos. 4~7 or 11~14 with the side chain of glutamic acid or lycine attached at the gamma position of the PNA backbone, the melting temperature of the self dimer is lower than that of the PNA probe of SEQ ID No. 1 (FIG. 2). Also, from the comparison of the detection PNA probes of SEQ ID Nos. 1~7 which form a hetero dimer with, and binds in anti parallel orientation to, the clamping probe of SEQ ID No. 23 with the detection PNA probes of SEQ ID Nos. 8~16 which bind in parallel orientation to the probe, it was found that hetero dimer is formed in the case of anti parallel binding, but that hetero dimer is not formed in the case of parallel binding (FIG. 3).

Figure 4:
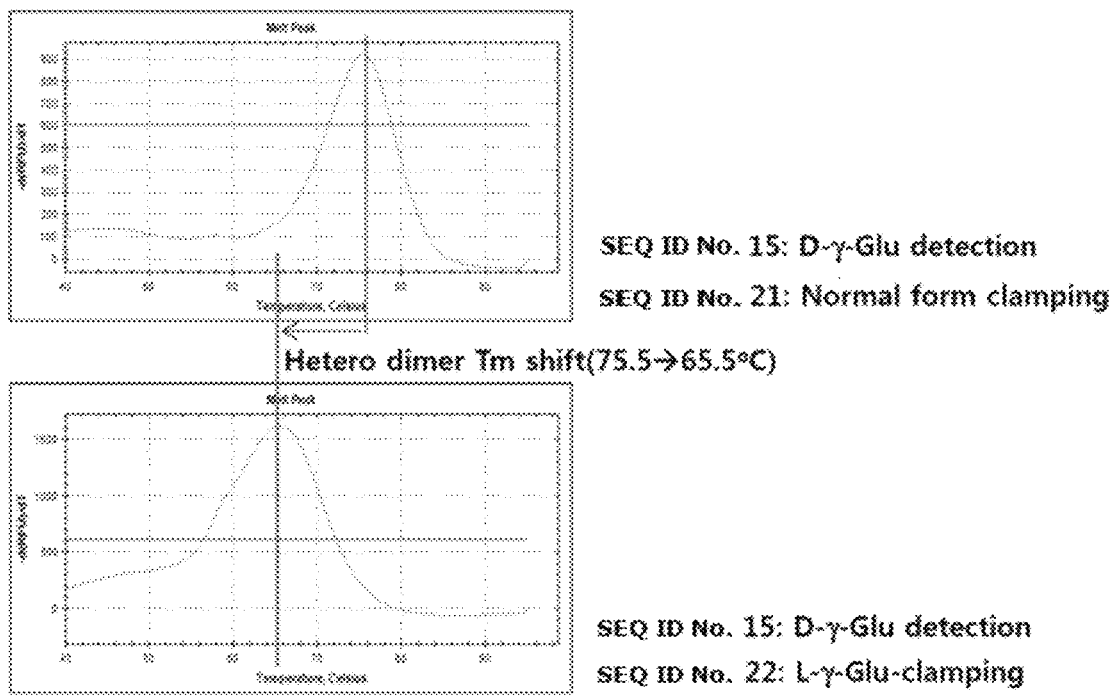
FIG. 4 shows graphs illustrating the decrease in melting temperature of the hetero dimer of a PNA detection probe imparted a three-dimensional structure and a PNA clamping probe imparted a three-dimensional structure.
Figure 5:
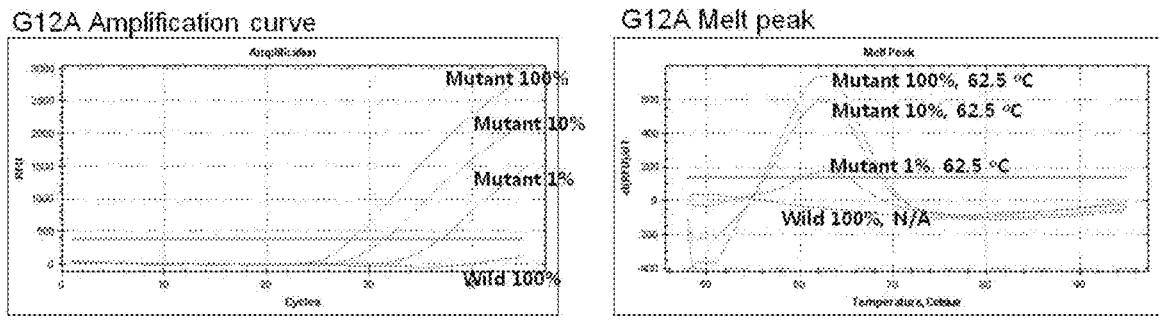
FIG. 5 shows graphs illustrating an amplification curve and melting curve of G12A, which is a K-ras gene mutant, using the PNA mixture of the present invention (SEQ ID No. 15).
Figure 6:
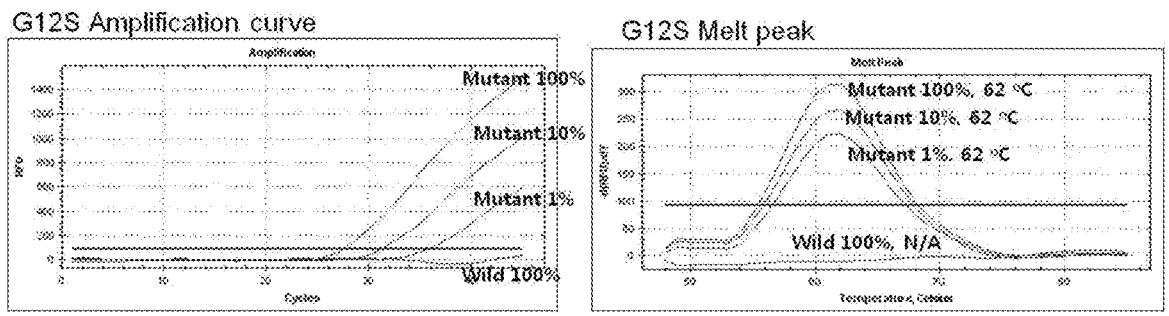
FIG. 6 shows graphs illustrating an amplification curve and melting curve of G12S, which is a K-ras gene mutant, using the PNA mixture of the present invention (SEQ ID No. 16).
Figure 7:
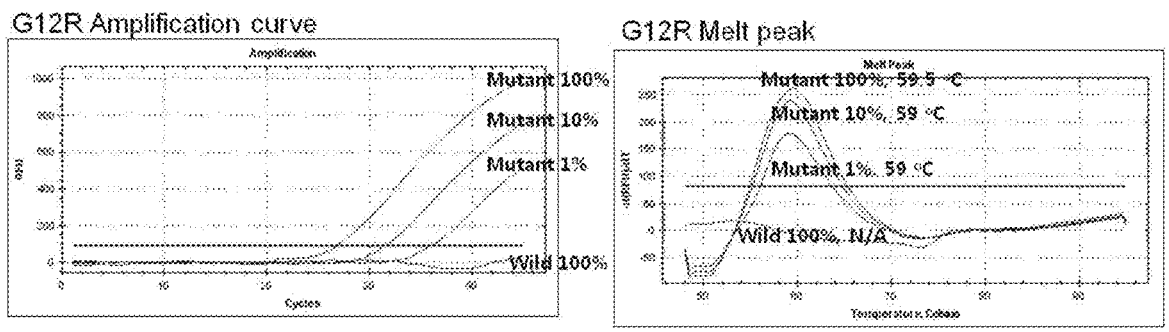
FIG. 7 shows graphs illustrating an amplification curve and melting curve of G12R, which is a K-ras gene mutant, using the PNA mixture of the present invention (SEQ ID No. 17).
Figure 8:
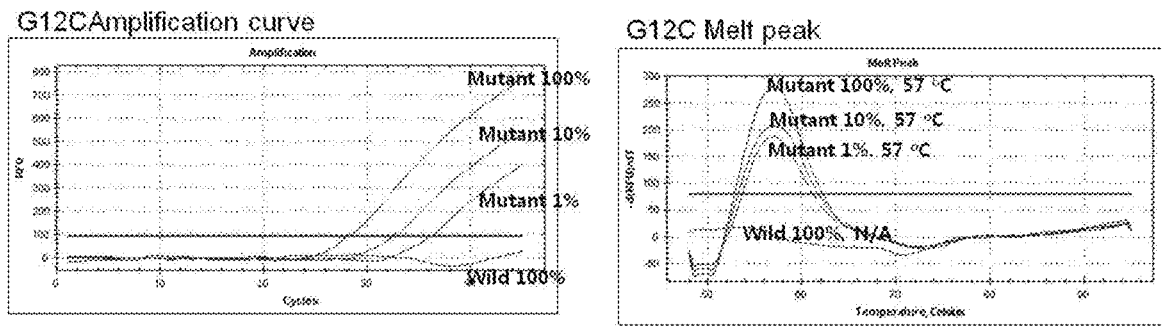
FIG. 8 shows graphs illustrating an amplification curve and melting curve of G12C, which is a K-ras gene mutant, using the PNA mixture of the present invention (SEQ ID No. 18).
Figure 9:
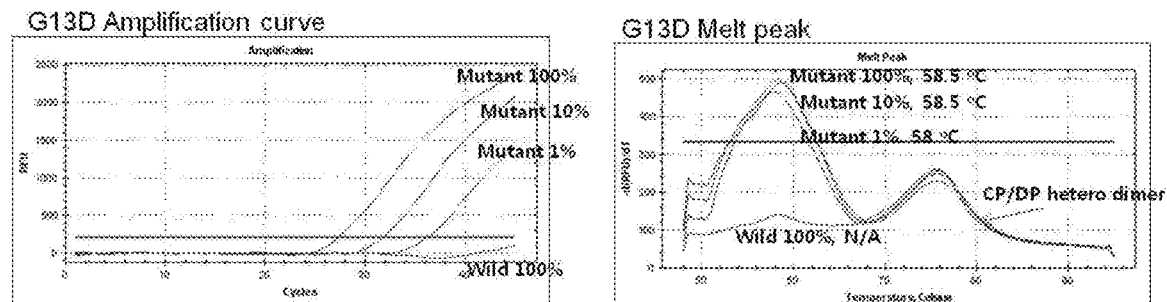
FIG. 9 shows graphs illustrating an amplification curve and melting curve of G13D, which is a K-ras gene mutant, using the PNA mixture of the present invention (SEQ ID No. 19).
Figure 10:
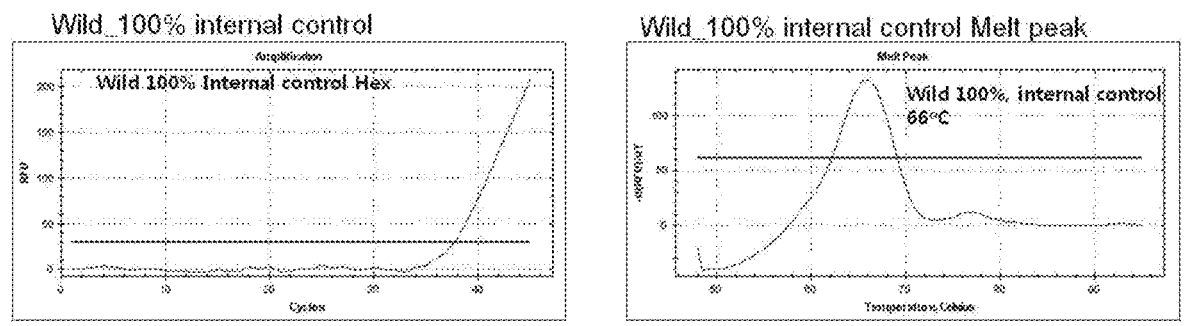
FIG. 10 shows graphs illustrating an amplification curve and melting curve of internal control using the PNA mixture of the present invention (SEQ ID No. 20).

Also, from the comparison of the clamping probe of SEQ ID No. 21 and the clamping probe of SEQ ID No. 22 with L-glutamic acid attached with the detection PNA probes of SEQ ID Nos. 15~19 in terms of the formation of hetero dimer, it was found that the melting temperature of hetero dimer decreases sharply when using the clamping probe of SEQ ID No. 22 with L-glutamic acid attached, when compared to the case of using the clamping probe of SEQ ID No. 21 which is not modified (FIG. 4).

When compared with the PNA probe of SEQ ID No. 1, the PNA probes of SEQ ID Nos. 3, 5 and 7 structurally modified (in terms of three-dimensional structure and electric charge) by attaching D-glutamic acid at the gamma position of the PNA backbone showed a great increase in the difference (ΔTm) of the melting temperature between the target DNA and single nucleotide mismatch DNA (Table 4). Also, it was confirmed that the PNA probe of the present invention with a modified structure has an increased specificity to single nucleotide variation, thereby achieving a difference in melting temperature of at 20° C. between the wild type gene and target nucleic acid gene, which allows to reduce non-specific binding in real-time amplification curve and problems that may occur in melting curve analysis.

In general, in order to detect a plurality of target nucleic acids simultaneously, the conventional methods for analyzing amplification curve using real-time PCR use a fluorescent substance to detect the target nucleic acid in a sample. Thus, the methods have a problem that as many probes having a fluorescent substance as the number of targets is required in order to detect at least two target nucleic acids, and thus have a limitation in multiple detection. However, the method for simultaneous detection of multiple target nucleic acids of the present invention can conduct an amplification curve analysis and a melting curve analysis simultaneously by using a probe mixture, and thus is capable of detecting multiple targets by using one fluorescent substance.

Also, the method for simultaneous detection of multiple target nucleic acids using the probe mixture of the present invention is not limited to simultaneous analysis of amplification curve and melting curve. It also enables a separate or sequential analysis of amplification curve and melting curve. The method also allows to detect target nucleic acids by performing only amplification curve analysis or melting curve analysis, as needed. Particularly, according to the method of the present invention, in case quantitative analysis is not required, by conducting only a curve analysis alone without an amplification curve analysis, the presence or genotype of the target nucleic acid can be determined.

Specifically, the method for simultaneous detection of multiple target nucleic acids of the present invention comprises: (a) mixing a probe mixture comprising a clamping probe and a detection probe and a primer with a test specimen including the target nucleic acids and hybridizing the mixture to obtain a real-time amplification curve; (b) obtaining a melting curve of the detection probe from the amplification product and detection probe complex by varying temperature after the amplification process; and (c) analyzing the real-time amplification curve and melting curve obtained separately, sequentially or simultaneously.

The clamping probe and detection probe in step (a) can be variously adjusted according to the number of target nucleic acids to be detected. In order to decrease the deviation of melting temperature depending on the concentration of the amplification product in the step of obtaining the melting curve, before the step of obtaining the melting curve, at least 5 PCR cycles can be added in addition to the step of obtaining real-time amplification curve. Preferably, 5~20 cycles can be added.

Also, as a detection method of the present invention, a method for simultaneous detection of multiple target nucleic acids comprising: (a) mixing a probe mixture comprising a clamping probe and a detection probe and a primer with a test specimen including the target nucleic acids and hybridizing the mixture to obtain a real-time amplification curve; and (b) analyzing the real-time amplification curve obtained, or a method for simultaneous detection of multiple target nucleic acids comprising: (a) mixing a probe mixture comprising a clamping probe and a detection probe and a primer with a test specimen including the target nucleic acids and hybridizing the mixture; (b) melting the hybridized product by varying temperature to obtain a melting curve; and (c) analyzing the melting curve obtained can be used.

The step of obtaining an amplification curve or melting curve in the present invention is performed through the real-time PCR (polymerase chain reaction), and the amplification curve analysis is characterized by measuring and analyzing the Ct (cycle threshold). If the target nucleic acid exists in the sample or a large amount of the target nucleic acid is included in the sample, the number of cycles required to reach the threshold decreases, thus resulting in a low Ct value. Thus, this analysis enables to confirm the presence of the target nucleic acid and to detect the amount of the initial target nucleic acid.

Also, in general, the melting curve analysis is performed lastly after the process of real-time PCR is completed. In this analysis, after lowering the temperature of the sample to around 30~55° C., magnitude of fluorescence signal is measured while increasing the temperature by 0.5~1° C. every second up to 95° C. When the temperature goes up, the detection probe and the target nucleic acid (one strand of the target nucleic acid that can complimentarily bind to the detection probe) are separated from each other, and then fluorescence is quenched, which results in a sharp decline in fluorescence signal. Accordingly, it is possible to confirm the presence of a target nucleic acid through the melting peak.

The method for simultaneous detection of multiple target nucleic acids of the present invention is characterized by detecting target nucleic acid included in an amount of 0.01% or 0.1%~100% in 10 ng or below of a nucleic acid sample.

The term "sample" in the present invention covers various samples. Preferably, biosamples are analyzed using the method of the present invention. Biosamples of the origin of plants, animals, human beings, fungus, bacteria and virus can be analyzed. In case of analyzing samples of the origin of mammals or human beings, the sample can be originated from a specific tissue or organ. Representative examples of the tissues include connective tissues, skin tissues, muscle tissues or nervous tissues. Representative examples of the organs include eye, brain, lung, liver, spleen, bone marrow, thymus, heart, lymph, blood, bone, cartilage, pancreas, kidney, gallbladder, stomach, small intestine, testis, ovary, uterus, rectum, nervous system, gland and internal vessel. The biosample to be analyzed includes any cell, tissue, or fluid of the biological origin or any medium that can be well analyzed by the present invention, which include samples obtained from foods produced to be consumed by human beings, animals or human beings and animals. Also, the biosample to be analyzed includes body fluid samples, which include blood, blood serum, plasma, lymph, breast milk, urine, human feces, eyeball fluid, saliva, semen, brain extract (for example, brain splinters), spinal fluid, and extracts from appendix, spleen, and tonsil tissues, but are not limited thereto.

The target nucleic acid of the sample is DNA or RNA, and the molecule may be in the form of a double strand or a single strand. In case the nucleic acid as an initial substance is double stranded, it is preferable to make the double strand into a single strand, or a partially single-stranded form. Well known methods for separating strands include heat treatment, alkali treatment, formamide treatment, urea treatment and glycoxal treatment, enzymatic methods (e.g., helicase action) and binding protein, but are not limited thereto. For example, strand separation can be achieved by a heat treatment to 80~105° C. General methods of the above treatments are disclosed in Joseph Sambrook et al, *Molecular Cloning*, 2001.

In an embodiment of the present invention, an experiment was performed using, as the target nucleic acids to be subjected to the simultaneous detection of multiple target nucleic acids, K-ras (V-Ki-ras2 Kirsten rat sarcoma viral oncogene homolog) gene, which is a representative somatic genes frequently mutated. Genes were separated from each cell line in Table 5, and samples were prepared to comprise 100%, 10%, 1%, or 0% of each mutant gene in the wild type gene (Table 6).

In order to confirm whether simultaneous multiple detection of the 5 types of mutant genes included in the wild type gene is possible, SEQ ID Nos. 15~19 in Table 1 as PNA detection probes, SEQ ID No. 22 as a PNA clamping probe, and SEQ ID No. 20 as an internal control (complementarily binding to wild type gene) were used. A reaction mixture solution of PNA probe and PCR primer was prepared by the method of Example 4-1, and real-time PCR reaction analysis and melting curve analysis were carried out for simultaneous analysis of multiple genotypes.

As a result of analyzing the real-time amplification curve and melting curve of wild type gene and K-ras mutant gene according to the method of the present invention, as shown in FIGS. 5~11, it was found that it is possible to not only simultaneously detect 1% of multiple K-ras mutant genes G12A, G12S, G12R, G12C and G13D included in wild type gene, but also to identify and quantify mutation genotypes.

Figure 11:
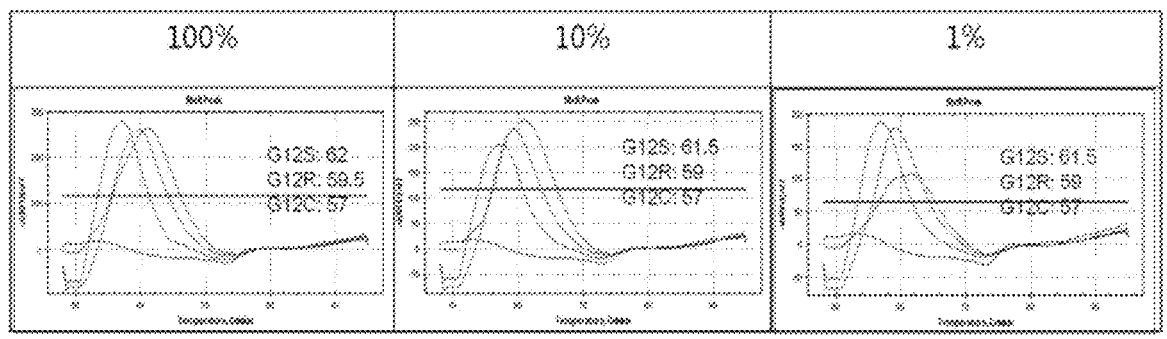
FIG. 11 shows graphs of the melting curve signals of the probes of SEQ ID Nos. 16, 17 and 18 according to the concentration of the targets G12S, G12R and G12C included in wild type gene. This shows that genotype can be determined by melting curve analysis of three types of K-ras mutant genes: G12S, G12R, G12C (SEQ ID Nos. 16, 17 and 18) with one fluorescence channel.

Also, as a result of analyzing the amplification curves of FIGS. 5~10, it was found that the amplification of 100% wild type gene is inhibited by the PNA clamping probe of the present invention. Also, it was confirmed that by using the difference in melting temperature among the mutation detection probes, various mutations can be detected simultaneously even with a small number of fluorescence channels (FIG. 11 and Table 8).

That is, the method for simultaneous detection of multiple target nucleic acids of the present invention structurally modifies a clamping probe and detection probe to decrease the melting temperature of self dimer or hetero dimer between probes and increase the specificity to single nucleotide variation, thereby allowing to simultaneously detect a trace of various multiple target nucleic acids and determine and quantify genotypes.

According to another aspect, the present invention relates to a kit for simultaneous detection of multiple target nucleic acids comprising a probe mixture comprising a clamping probe and a detection probe and using the method for simultaneous detection of multiple target nucleic acids of the present invention.

According to the present invention, the kit can simultaneously detect various target nucleic acids included in an amount of 1~100% in the sample and can be used for analyzing the quantity or genotype of the target nucleic acid.

The kit of the present invention may optionally comprise a reagent required for carrying out target amplification PCR (for example, PCR), such as buffer, DNA polymerase cofactors and deoxyribonucleotide-5-triphosphate. Also, the kit of the present invention may optionally comprise various polynucleotide molecules, reverse transcriptase, various buffers and reagents, and antibodies inhibiting DNA polymerase activity.

Also, the optimum amount of the reagents of the kit in specific reactions can be easily determined by a person having ordinary skill in the art who learned the disclosures in the present specification. Typically, the kit of the present invention is manufactured as a separate package or compartment comprising the ingredients mentioned above.

EXAMPLES

Hereinafter, the present invention will be explained in more detail with reference to the examples. These examples are only to exemplify the present invention, and it is obvious to a person having ordinary skill in the art that the scope of the present invention is not interpreted to be limited by the examples.

Probe Mixture System Comprising a Clamping Probe and a Detection Probe Hybridizing to Complementary Strands Example 1

Synthesis of PNA Probe and Target DNA Oligomer Used for the Detection of Mutation 1-1: Production of PNA Probes In order to demonstrate the feasibility of the method for detecting mutation using a PNA mixture comprising a detection probe and a clamping probe structurally modified by changing the three-dimensional structure or imparting electric charge, etc., as can be seen in Table 1, PNA probes with a negatively charged L-glutamic acid or D-glutamic acid, an uncharged L-alanine or D-alanine, or a positively charged L-lysine or D-lysine attached at the gamma position of the PNA probe skeleton, as shown in Table 1, were synthesized.

TABLE 1

Sequence of PNA probes used in the present invention

| SEQ ID No. | Name of PNA | N-term | PNA Sequence (N→C) | C-term |
|---|---|---|---|---|
| 1 | K12-G | ROX | acgccagcagctc | OEK(dabcyl) |
| 2 | K12-G-L-ala | ROX | acgccagc①gc②c | OEK(dabcyl) |
| 3 | K12-G-D-ala | ROX | acgccagc⑤gc⑥c | OEK(dabcyl) |
| 4 | K12-G-L-Glu | ROX | acgccagc1gc2c | OEK(dabcyl) |
| 5 | K12-G-D-Glu | ROX | acgccagc5gc6c | OEK(dabcyl) |
| 6 | K12-G-L-Lys | FAM | acgccagc(1)gc(2)c | OEK(dabcyl) |
| 7 | K12-G-D-Lys | FAM | acgccagc(5)gc(6)c | OEK(dabcyl) |
| 8 | K12-G-pa | Dabcyl | ctcgacgaccgca | OEK(ROX) |
| 9 | K12-G-L-ala-pa | Dabcyl | c②cg①cgaccgca | OEK(ROX) |
| 10 | K12-G-D-ala-pa | Dabcyl | c⑥cg⑤cgaccgca | OEK(ROX) |
| 11 | K12-G-L-Glu-pa | Dabcyl | c2cg1cgaccgca | OEK(ROX) |
| 12 | K12-G-D-Glu-pa | Dabcyl | c6cg5cgaccgca | OEK(ROX) |
| 13 | K12-G-L-Lys-pa | Dabcyl | c(2)cg(1)cgaccgca | OEK(FAM) |
| 14 | K12-G-D-Lys-pa | Dabcyl | c(6)cg(5)cgaccgca | OEK(FAM) |
| 15 | SW1116-G12A-62-AP15 | Dabcyl | GG5GC6GCTGGCGTA | OEK(ROX) |
| 16 | A549-G12S-58-AP13 | Dabcyl | G7AG8TAGTGGCG | OEK(FAM) |
| 17 | xxx-G12R-61-AP13 | Dabcyl | G7AG8TCGTGGCG | OEK(FAM) |
| 18 | MIAPaCa2-G12C-58-AP13 | Dabcyl | G7AG8TTGTGGCG | OEK(FAM) |
| 19 | LoVo-G13D-61-AP15 | Dabcyl | G8TG7TGACGTAGGC | OEK(CY5) |
| 20 | Internal control | Dabcyl | GCGGTGG2CG1GG | OEK(HEX) |
| 21 | K12, 13 CP | | CCTACGCCACCAGCTCC | |
| 22 | K12, 13 CP glu | | CCTACGCCACC1GC2CC | |
| 23 | K12 down CP | | GGAGCTGGTGGCGTAGGCA | |

(The numbers in the PNA sequences of table 1 indicate a modification of part of the PNA sequence to L-glutamine, D-glutamine, L-alanine, D-alanine, L-lysine, or D-lysine. For more details, refer to Table 2.)

TABLE 2

Modification of PNA sequence

| Form | Base | Mark | Form | Base | Mark | Form | Base | Mark |
|---|---|---|---|---|---|---|---|---|
| L-glutamic acid | A | 1 | L-alanine | A | ① | L-lysine | A | (1) |
|  | T | 2 |  | T | ② |  | T | (2) |
|  | G | 3 |  | G | ③ |  | G | (3) |
|  | C | 4 |  | C | ④ |  | C | (4) |
| D-glutamic acid | A | 5 | D-alanine | A | ⑤ | D-lysine | A | (5) |
|  | T | 6 |  | T | ⑥ |  | T | (6) |
|  | G | 7 |  | G | ⑦ |  | G | (7) |
|  | C | 8 |  | C | ⑧ |  | C | (8) |

PNA probe was synthesized by performing a solid phase synthesis from a PNA monomer protected with benzothiazolesulfonyl (Bts) and functionalized resin according to the method disclosed in Korean Patent No. 464261 (Lee et al., *Org. Lett.*, 9:3291, 2007). Otherwise, PNA can be synthesized by the known 9-flourenylmethoxycarbonyl (Fmoc) or t-Boc (t-butoxycarbonyl) synthesis method (Kim L. et al., *J. Org. Chem.*, 59:5767, 1994; Stephen A. et al., *Tetrahedron*, 51:6179, 1995). A reporter substance and quencher substance were attached to the PNA probe according to a method widely known in the pertinent art.

PNA probes of SEQ ID Nos.: 1~7 & 15~19 are detection probes, and are designed to detect mutation. PNA probes of SEQ ID Nos.: 8~14 are produced as parallel binding detection probes.

1-2: Production of DNA Oligomers

In order to analyze the characteristics of the PNA probes produced in Table 1 above, the target DNA oligomers (Table 3) binding to the PNA probes, synthesized by Bioneer Corporation (Korea), were used.

TABLE 3

DNA oligomer sequences for analyzing characteristics of PNA probe

| SEQ ID No. | Name | Sequence (5' → 3') |
|---|---|---|
| 24 | >5-up 0C | GTAGTTGGAGCTGCTGGCGTAGGCAAG |
| 25 | >1-up wild | GTAGTTGGAGCTGGTGGCGTAGGCAAG |

PNA probes corresponding to SEQ ID Nos.: 1~14 in Table 1 are completely hybridized with SEQ ID No. 24 (>5-up 0C) in Table 3, but not completely hybridized with SEQ ID No. 25 (1-up wild) (single nucleotide mismatch).

Example 2

Analysis of Characteristics of PNA Probe Using Melting Curve Analysis

In order to analyze the formation of self dimer and hetero dimer and the specificity of the PNA probes produced in Example 1-1, 0.5 µM of a PNA probe in Table 1 above, 0.5 µM of a DNA oligomer in Table 3, and PCR amplification solution (Enzynomics, Korea) were mixed. The mixture was subjected to a denaturation step for 5 minutes at 95° C. in a real-time PCR machine (CFX96TM Real-time PCR System, Bio-Rad, U.S.A.). Then, the mixture was cooled down to 30° C. and then hybridized for 5 minutes. Thereafter, a melting curve analysis was performed by measuring fluorescence while increasing the temperature by 0.5° C. from 30° C. to 95° C.

As a result, it was found that when compared with the PNA probe of SEQ ID No. 1, the probes of SEQ ID Nos. 4, 5, 6 and 7 with glutamic acid or lysine attached and the probes of SEQ ID Nos. 11, 12, 13 and 14 with glutamic acid or lysine which bind in parallel orientation, showed a decrease in the melting temperature of the self dimer. Comparison results of SEQ ID Nos. 1 and 4 are shown in FIG. 2 as an example.

From the comparison of the detection PNA probes of SEQ ID Nos. 1~7 which form a hetero dimer with and bind in anti parallel orientation to the clamping probe of SEQ ID No. 23 with the detection PNA probes of SEQ ID Nos. 8~16 which bind in parallel orientation, it was found that hetero dimer is formed in the case of anti parallel binding, but that hetero dimer is not formed in the case of parallel binding. As an example, comparison results of the formation of hetero dimer between SEQ ID Nos. 1 and 23 and SEQ ID Nos. 8 and 23 are shown in FIG. 3.

From the comparison of the clamping probe of SEQ ID No. 21 forming a hetero dimer with the detection PNA probes of SEQ ID Nos. 15~19 with the clamping probe of SEQ ID No. 22 with L-glutamic acid attached, it was found that the melting temperature of the hetero dimer decreases sharply when the clamping probe of SEQ ID No. 22 with L-glutamic acid attached is used, when compared with the case of using the non-modified clamping probe of SEQ ID No. 21. As an example, the comparison results of the formation of hetero dimer between SEQ ID Nos. 15 and 21 and SEQ ID Nos. 15 and 22 are shown in FIG. 4. Also, it was confirmed that the melting temperature of hetero dimer decreased by about 10° C. (Tm: 75.5° C.→65.5° C.) when the clamping probe of SEQ ID No. 22 is used, when compared with the case of using the clamping probe of SEQ ID No. 21.

TABLE 4

Comparison of melting temperature of PNA probes imparted with a three-dimensional structure from single nucleotide mismatching sequence.

| | Melting temperature (° C.) from perfect match SEQ ID No. 24 | Melting temperature (° C.) from single nucleotide mismatch SEQ ID No. 25 | Difference (ΔTm) |
|---|---|---|---|
| SEQ ID No. 1 | 75 | 58.5 | 16.5 |
| SEQ ID No. 3 | 63 | 34 | 29 |
| SEQ ID No. 5 | 58 | 35 | 23 |
| SEQ ID No. 7 | 61 | 36.5 | 24.5 |

Also, it was found that when compared with the PNA probe of SEQ ID No. 1, the PNA probes of SEQ ID Nos. 3, 5 and 7 structurally modified (in terms of three-dimensional structure and electric charge) by attaching D-glutamic acid at the gamma position of the PNA backbone show a sharp increase in the difference (ΔTm) in the melting temperature thereof between the target DNA and the DNA with single nucleotide showing mismatch (Table 4). As such, the PNA probe with a modified structure of the present invention has an increased specificity to single nucleotide variation so that the difference in the melting temperature between the wild-type gene and mutant gene is at least 20° C., which enables to solve the problem of the occurrence of non-specific signal in the analysis of melting curve and amplification curve.

Example 3

Production of a Target Nucleic Acid and Primer for Simultaneous Detection of Multiple Somatic Mutations Experiments were carried out using, as the target nucleic acid for simultaneous detection of multiple somatic mutations, K-ras (V-Ki-ras2 Kirsten rat sarcoma viral oncogene homolog) gene, which is a representative somatic gene frequently mutated. One wild-type cell line (HeLa) of wild-type K-ras codons 12 and 13, and 5 mutant cell lines (SW-1116, A549, SW48, MIA PaCa2, LoVo) were obtained from by the Korean Cell Line Bank (Table 5).

TABLE 5

Position of K-ras mutations and mutant cell lines

| Cell line name | base change | Exon | Mutation | KCLB No. |
|---|---|---|---|---|
| HeLa | wild | — | wild | |
| SW-1116 | 35 G > C | 2 | Gly12Ala (G12A) | 10233 |
| A549 | 34 G > A | 2 | Gly12Ser (G12S) | 10185 |
| SW48 (K-RAS mutant) | 34 G > C | 2 | Gly12Arg (G12R) | — |

TABLE 5-continued

Position of K-ras mutations and mutant cell lines

| Cell line name | base change | Exon | Mutation | KCLB No. |
|---|---|---|---|---|
| MIA PaCa2 | 34 G > T | 2 | Gly12Cys (G12C) | 21420 |
| LoVo | 38 G > A | 2 | Gly13Asp (G13D) | 10229 |

The cell lines obtained were cultured in an incubator at 37° C., and 5% carbon dioxide ($CO_2$) using a medium obtained by adding 10% heat-inactivated fetal bovine serum (FBS, Hyclone, Thermo scientific, USA) and 1× penicillin-streptomycin (Welgene, Korea) to RPMI1640 (Hyclone, Thermo scientific, USA). The target nucleic acids were obtained by extracting DNA from the cultured cell lines by using the Labopass™ tissue mini kit (Cosmogenetech, Korea) based on the manual provided by the kit. Samples were prepared so that the wild-type gene obtained above comprises 100%, 10%, 1%, or 0% of each mutant gene (Table 6).

TABLE 6

Amounts of target nucleic acid used in the reaction

| | Wild gDNA | Mutant gDNA |
|---|---|---|
| Mutant 100% | 0 ng | 25 ng |
| Mutant 10% | 25 ng | 2.5 ng |
| Mutant 1% | 25 ng | 0.25 ng |
| Mutant 0% | 25 ng | 0 ng |

TABLE 7

Primer sequences for implementing both inhibition and detection simultaneously

| SEQ ID No. | Name | Sequence (5' → 3') |
|---|---|---|
| 26 | BJC2005-F | AAGGCCTGCTGAAAATGACT |
| 27 | BJC2005-R | GGTCCTGCACCAGTAATATGCA |

Also, primers for simultaneously implementing both inhibition and detection of K-ras gene in Table 5 were synthesized by Bioneer Corporation (Korea) (Table 7).

Example 4

Real-Time PCR and Simultaneous Analysis of Multiple Genotypes Using Melting Curve 4-1: Preparation of a Mixed Solution of PNA Probe and PCR Primer for Simultaneous Detection of Multiple Somatic Mutations To carry out simultaneous detection of multiple somatic mutations, a mixed solution of PNA probe was prepared by mixing the same amount of the PNA probe of SEQ ID No. 1 in Table 1 diluted to a concentration of 13.5 μM, the PNA probes of SEQ ID Nos. 16~18 diluted to a concentration of 18 μM, the PNA probes of SEQ ID No. 19 diluted to a concentration of 9 μM, the PNA probe of SEQ ID No. 20 diluted to a concentration of 18 μM, and the PNA probe of SEQ ID No. 22 diluted to a concentration of 4.5 μM. Then, the same amount of a forward primer of SEQ ID No. 26 diluted to a concentration of 1.5 μM and a reverse primer of SEQ ID No. 27 diluted to a concentration of 20 μM was mixed.

SEQ ID Nos. 15~19 were used as probes for mutation detection, SEQ ID No. 20 was used as an internal control, and SEQ ID No. 22 was used as a clamping probe.

A mixed reaction solution of PNA probes and PCR primers capable of simultaneous detection of 5 types of somatic mutations and analysis of mutation genotypes was prepared by mixing the mixed solution of PNA probes and mixed solution of primers in a ratio of 6:4.

4-2: Real-Time PCR and Melting Curve Analysis for Simultaneous Analysis of Multiple Genotypes After mixing 10 μl of a mixed solution of PNA probes and PCR primers prepared in Example 4-1 and 10 μl of PCR amplification solution and adding 5 μl of each target nucleic acid produced in Example 3 (Table 5, Table 6) thereto, real-time PCR was performed (Real-time PCR machine, CFX96™ Real-time PCR System, Bio-Rad, U.S.A.). After a reaction of 15 minutes at 95° C., 45 cycles were run with 10 seconds at 95° C., 7 seconds at 76° C., 20 seconds at 53° C., and 20 seconds at 72° C. Fluorescence was measured at 53° C. Then, the PCR was completed by repeating 10 cycles with 10 seconds at 95° C., 7 seconds at 76° C., 20 seconds at 53° C., and 20 seconds at 72° C. without measuring fluorescence. After completing the PCR cycles, and going through a denaturation step for 5 minutes at 95° C., the mixture was cooled down to 48° C. and then hybridized for 5 minutes. Then, a melting curve analysis was performed by measuring fluorescence while increasing the temperature by 0.5° C. from 48° C. to 95° C.

The amplification curve and melting curve obtained for each target nucleic acid are shown in FIGS. 5~10. The analysis results of the melting curves of each PNA probe from the matching target nucleic acid for genotyping are shown in Table 8. Also, the results of incorporating the melting curves of G12S, G12R and G12C with a single channel are shown in FIG. 11.

TABLE 8

Analysis values of melting curves of wild-type and K-ras mutations

| SEQ ID No. of PNA probe | Mutation | Fluorescence | Tm (° C.) 60 cycle | Error range (° C.) |
|---|---|---|---|---|
| 15 | G12A | ROX | 62.5 | ±0.5 |
| 16 | G12S | FAM | 62 | ±0.5 |
| 17 | G12R | | 59.5 | ±0.5 |
| 18 | G12C | | 57 | ±0.5 |
| 19 | G13D | Cy5 | 58.5 | ±0.5 |
| 20 | IC(wild) | HEX | 66 | ±0.5 |

As a result of analyzing the melting curves of wild-type and K-ras mutations, it was found that 1% of multiple K-ras mutant genes G12A, G12S, G12R, G12C, G13D included in wild-type can be detected simultaneously.

Also, from the amplification curve analysis of the detection probe of SEQ ID No. 20 complementary to the K-ras wild-type gene, it was confirmed that amplification of wild-type gene can be inhibited by the structurally modified PNA clamping probe of the present invention. This also supports the validity of the PCR assay.

Example 5

Detection of Somatic Mutation by MGB-Taqman Detection-PNA Clamping

In order to confirm whether somatic mutation can be detected even in case the detection probe of the present invention is a nucleic acid analogue other than PNA, EGFR mutation was detected using MGB-taqman as a detection probe.

5-1: Preparation of a Target Nucleic Acid with Somatic Mutation

A wild-type cell line, A549, was obtained from the Korean Cell Line Bank and an EGFR mutated cell line, H1975, was obtained from ATCC to prepare a target nucleic acid (Table 9).

TABLE 9

Position of EGFR mutation and mutated cell line

| Cell line name | base change | Exon | Mutation |
|---|---|---|---|
| A549 | wild | — | wild |
| H1975 | 2369C > T | 20 | Thr790Met |

The target nucleic acid was prepared and obtained in the same manner as in Example 3. Samples were prepared so that the wild-type gene comprises 100%, 10%, 1%, and 0% of each mutant gene.

5-2: Preparation of a Mixed Solution of PNA Probes and PCR Primers for Simultaneous Detection of Multiple Somatic Mutations The primers (SEQ ID Nos. 28 and 29) for mutation detection synthesized by Bioneer Corporation (Korea) (Table 10), and the MGB-taqman probe (SEQ ID No. 30) for detecting mutation synthesized by ABI (Applied Biosystems, USA) (Table 11) were used. PNA clamping probe was synthesized in the same manner as the method in Example 1.

TABLE 10

Base sequences of primers and MGB-taqman detection probe

| SEQ ID No. | Name | Sequence (5'→3') |
|---|---|---|
| 28 | T790M-forward | TCCACCGTGCAGCTCATC |
| 29 | T790M-reverse | GTCTTTGTGTTCCCGGACAT |
| 30 | T790M-detection probe MGB-taqman | VIC-AGCTGCATGATGAG-MGB-NFQ |

TABLE 11

Base sequence of PNA clamping probe

| SEQ ID No. | PNA Name | PNA Probe sequence N-term (N→C) | C-term |
|---|---|---|---|
| 31 | T790M clamping probe | K GCTCATCACGCAGCT CA | |

In order to confirm whether the system of MGB-taqman probe for detecting mutation and PNA probe for clamping wild type is capable of detection and clamping on different strands, real-time PCR was performed after adding 1.6 μM of forward primer (SEQ ID No. 28), 0.4 μM of reverse primer (SEQ ID No. 29), 0.8 μM of MGB-taqman probe (SEQ ID No. 30), 4 μM of PNA clamping probe (SEQ ID No. 31), 10 μl of PCR amplification solution specified in Example 4, and 5 μl of each target nucleic acid produced in Example 5-1 to an entire volume of 25 μl (Real-time PCR machine, CFX96TM Real-time PCR System, Bio-Rad, U.S.A.).

After a reaction of 15 minutes at 95° C., 45 cycles were repeated with 10 seconds at 95° C., 20 seconds at 60° C., and 20 seconds at 72° C. Fluorescence was measured at 60° C. As a result, it was confirmed from a real-time amplification curve analysis that the system of MGB-taqman probe for detecting mutation and PNA probe for clamping wild type operates on different strands. The results are shown in FIG. 12.

Probe Mixture System Comprising a Clamping Probe and a Detection Probe Competitively Hybridizing on the Same Strand

Example 6

Preparation of PNA Probes Used for Mutation Detection and Analysis of the Characteristics Thereof 6-1: Production of PNA Probes In order to detect mutation using a PNA mixture comprising a detection probe and clamping probe structurally modified by changing the three-dimensional structure or imparting electric charge to PNA probe and PNA, PNA probes were synthesized as shown in Table 12.

TABLE 12

Sequence of PNA probe used in the present invention

| SEQ ID No. | PNA name | PNA Sequence N-term (N→C) | C-term |
|---|---|---|---|
| 32 | G12D S1 | Dabcyl gac④tg①tggcgt | OEK(ROX) |
| 33 | G12D S2 | Dabcyl ga③ctg①tggcgt | OEK(ROX) |
| 34 | G12V S1 | Dabcyl gg①gc②gttggcgt | OEK(ROX) |
| 35 | K12 Clamping-1 | atctggtggcgtaggca | |
| 36 | K12 Clamping-2 | ctggtggcgtaggca | |
| 37 | G12D N2 | Dabcyl TGGAGCTGATG | OEK(FAM) |
| 38 | G12VN2 | Dabcyl TGGAGCTGTTG | OEK(ROX) |

(The numbers in the PNA sequence of Table 12 indicate a modification of part of the PNA sequence to D-glutamine. For more details, refer to Table 13.)

TABLE 13

Modification of PNA sequence

| Form | Base | Mark |
|---|---|---|
| D-glutamic acid | A | ① |
|  | T | ② |
|  | G | ③ |
|  | C | ④ |

As the detection probe for detecting K-ras mutant genotype, probes obtained by attaching a side chain of negatively charged D-glutamic acid at the gamma position of the backbone of a non-modified PNA or PNA probe were used. Also, a wild-type clamping probe were designed so as to bind in the same orientation to allow competitive binding against detection probe.

6-2: Analysis of PNA Probe Specificity Using Melting Curve Analysis

The binding specificity of the PNA probe sequences produced in Table 12 to DNA targets was analyzed through melting curve analysis, after mixing 10 μM of PNA detection probe and 4 μM PNA wild-type clamping probe, target DNAs and a PCR amplification solution (Enzynomics, Korea), and performing PCR. Real-time PCR machine (CFX96™ Real-time PCR System, Bio-Rad, U.S.A.) was used for PCR. As a result, probes were identified whose melting curves are distinguished according to the PNA probe sequence match rate to the target. It was confirmed from graphs that the detection probes of SEQ ID Nos. 33, 34 37 and 38 have excellent specificity to the base sequences of target DNAs (FIGS. 13, 14, and 15). Examples of Tm analysis results showing the temperatures at which a PNA probe melts from a target with a perfect match sequence or from targets with mismatch sequences are shown in Table 14.

TABLE 14

Comparison of single nucleotide specificity (Tm) between PNA and PNA probes imparted with a three-dimensional structure

| SEQ ID No. | Melting temperature (° C.) from perfect match | Melting temperature (° C.) from single nucleotide mismatch | | |
|---|---|---|---|---|
| 33 | G12D(G<u>A</u>T) 58° C. | G12A(GC<u>T</u>) 43° C. | G12V(G<u>TT</u>) 40° C. | G12S(<u>A</u>GT)<35° C. |
| 34 | G12V(G<u>TT</u>) 60° C. | G12D(G<u>A</u>T) 48° C. | G12A(GC<u>T</u>) 46° C. | G12S(<u>A</u>GT) 39° C. |
| 37 | G12D 60° C. | G12A 51° C. | G12V 51.5° C. | G12R 44.5° C. |
| 38 | G12V 65° C. | G12D 54.5° C. | G12S 50.5° C. | G12R 48.5° C. |

Example 7

Production of Target Nucleic Acids and Primers for Detection of Somatic Mutation Target nucleic acids were obtained and produced in the same manner as in Example 3. Samples were prepared so that the wild-type gene comprises 1%, 0.1%, 0.01% or 0% of each mutant gene (Table 15).

TABLE 15

Amount of target nucleic acid used in the reaction

| | Wild gDNA | Mutant gDNA |
|---|---|---|
| Mutant 1% | 25 ng | 250 pg |
| Mutant 0.1% | 25 ng | 25 pg |

TABLE 15-continued

Amount of target nucleic acid used in the reaction

| | Wild gDNA | Mutant gDNA |
|---|---|---|
| Mutant 0.01% | 25 ng | 2.5 pg |
| Mutant 0% | 25 ng | 0 ng |

Also, the primer for detecting K-ras genes in Table 15 was designed as shown in Table 16. Primers synthesized by Bioneer Corporation (Korea) were used.

TABLE 16

Primer sequences for improving detection sensitivity

| SEQ ID No. | Name | Base sequence (5' → 3') |
|---|---|---|
| 39 | G12/13 F1 | AGGTACTGGTGGAGTATTTG |
| 40 | G12/13 F2 | GTGACATGTTCTAATATAGTCAC |
| 41 | G12/13 RC1 | GTTCTAAATGGAGATAACAACC |
| 42 | G12/13 RC2 | TAGCAGTTCCGTGAGAACGGATGC |

Example 8

Improvement of Detection Sensitivity of a Method for Simultaneous Analysis of Multiple Genotypes Using Real-Time PCR and Melting Curve Analysis 8-1: Preparation of a Mixed Solution of PNA Probes and PCR Primers for Simultaneous Detection of Multiple Somatic Mutations and Improvement of the Detection Sensitivity To carry out simultaneous detection of multiple somatic mutations and improve the detection sensitivity thereof, a mixed solution of PNA probes was prepared by diluting the probes in Table 12 so that the PNA probes of SEQ ID No. 35 or 36 have a concentration of 4 μM, and the PNA probes of SEQ ID Nos. 32~34 and 37~38 have a concentration of 10 μM. Then, each primer was diluted so that the forward primers of SEQ ID Nos. 39 and 40 have a concentration of 3 μM, and the reverse primers of SEQ ID Nos. 41 and 42 have a concentration of 10 μM. Then, the results of each primer were observed.

The target nucleic acid produced in Table 15 is used to determine the presence of somatic mutation and measure the detection sensitivity (FIGS. 13, 14 and 15).

8-2: Measurement of Detection Sensitivity Through Real-Time PCR and Melting Curve Analysis After mixing 10 μl of a mixed solution of PNA probe and PCR primer prepared in 8-1, and 10 μl of PCR amplification solution (Enzynomics, Korea), 5 μl of the prepared target DNA specimen was added to perform real-time PCR (Real-time PCR machine, CFX96TM Real-time PCR System, Bio-Rad, U.S.A.). The PCR was performed in the three steps of clamping, detecting and melting. After a reaction of 15 minutes at 95° C., 15 cycles were run with 30 seconds at 95° C., 20 seconds at 70° C., 30 seconds at 63° C., and 30 seconds at 72° C., without measuring fluorescence, and 40 cycles were repeated with 10 seconds at 95° C., 20 seconds at 53° C., and 20 seconds at 72° C., measuring fluorescence at 53° C. Then, after maintaining the mixture for 15 minutes at 95° C., the mixture was cooled down to 35° C. and hybridized for 5 minutes. Then, melting curve analysis was performed by measuring fluorescence while increasing the temperature by 0.5° C. from 35° C. to 75° C.

As a result, it was found that the melting temperature of the detection probe of SEQ ID No. 33 from the target DNA is different between G12A, G12D, G12S and G12V (FIG. 13(A)). Also, the melting temperature of the detection probe of SEQ ID No. 34 from the target DNA is different between G12A, G12D, G12S and G12V (FIG. 13(B)). Thus, it was confirmed that multiple mutant genes can be detected even with one detection probe.

That is, it was confirmed that the system in which the detection probe and clamping probe are designed to bind to the same strand so as to competitively react with the target can also simultaneously detect multiple K-ras mutant genes of G12A, G12D, G12V, G12S, G12R, and G12C with only two fluorescences (reporters) in one tube by using the difference of the melting temperature of the mutation detection probes.

Also, mutant genes (G12D, G12V) were sequentially diluted in 25 ng of the wild-type gene (HeLa cell) obtained, so that samples were prepared to contain 1%, 0.1%, 0.01%, or 0% of each mutant gene (G12D, G12V) in the wild type gene. For the purpose of this preparation, $10^4$ copies of mutant genes were defined as 100%. Then, PCR was performed by the above method. As a result, it was found that the amplification of the wild-type gene is inhibited by the PNA clamping probe of the present invention, and that even mutation included in an amount of 0.01% can be detected (FIG. 14).

The above disclosure describes certain parts of the invention in detail. Thus, it is obvious to a person having ordinary skill in the art that the detailed disclosures are merely to illustrate preferable embodiments, and that the scope of the present invention is not limited by the disclosure. Thus, the substantial scope of the present invention is defined by the attached claims and equivalents thereto.

What is claimed is:

1. A probe mixture for real-time detection and simultaneous multiple detection of target nucleic acids comprising at least one detection probe and at least one clamping probe for inhibiting amplification of wild type genes or unwanted genes where an amino acid or a side chain of the amino acid is attached to the detection probe or clamping probe to structurally modify the probe such that a mutation can be detected with 0.01% sensitivity by simultaneously analyzing a real-time amplification curve and a melting curve, wherein the amino acid is selected from the group consisting L-glutamic acid, and D-glutamic acid.

2. The probe mixture according to claim 1, wherein the detection probe or clamping probe is a nucleic acid analogue selected from the group consisting of oligonucleotides, peptide nucleic acids (PNA) and locked nucleic acids (LNA).

3. The probe mixture according to claim 1, wherein the amino acid is attached at the N terminus or C terminus of the probe.

4. The probe mixture according to claim 1, wherein the side chain of the amino acid is attached at the alpha, beta or gamma position of the probe backbone.

5. The probe mixture according to claim 1, wherein a reporter and a quencher are attached to the detection probe.

6. The probe mixture according to claim 5, wherein the reporter is at least one fluorescent material selected from a group consisting of fluorescein, fluorescein chlorotriazinyl, rhodamine green, rhodamine red, tetramethylrhodamine, FITC, Oregon green, Alexa Fluor, FAM, JOE, ROX, HEX, Texas Red, TET, TRITC, TAMRA, cyanine-based dye and thiadicarbocyanine dye.

7. The probe mixture according to claim 5, wherein the quencher is at least one selected from a group consisting of Dabcyl, TAMRA, Eclipse, DDQ, QSY, Blackberry Quencher, Black Hole Quencher, Qxl, Iowa black FQ, Iowa black RQ, and IRDye QC-1.

8. A method for simultaneous detection of multiple target nucleic acids using a probe mixture for real-time detection of target nucleic acids comprising at least one detection probe and at least one clamping probe for inhibiting amplification of wild type genes or unwanted genes where an amino acid or a side chain of the amino acid is attached to the detection probe or clamping probe to structurally modify the probe comprising detecting a mutation with 0.01% sensitivity by simultaneously analyzing a real-time amplification curve and a melting curve, wherein the amino acid is selected from the group consisting of L-glutamic acid, and D-glutamic acid.

9. The method according to claim 8, wherein the detection probe or clamping probe is a nucleic acid analogue selected from a group consisting of oligonucleotides, peptide nucleic acids (PNA) and locked nucleic acids (LNA).

10. The method according to claim 8, wherein the amino acid is attached at the N terminus or C terminus of the probe.

11. The method according to claim 8, wherein the side chain of an amino acid is attached at the alpha, beta or gamma position of the probe backbone.

12. The method according to claim 8, wherein a reporter and a quencher are attached to the detection probe.

13. The method according to claim 12, wherein the reporter is at least one fluorescent material selected from a group consisting of fluorescein, fluorescein chlorotriazinyl, rhodamine green, rhodamine red, tetramethylrhodamine, FITC, Oregon green, Alexa Fluor, FAM, JOE, ROX, HEX, Texas Red, TET, TRITC, TAMRA, cyanine-based dye and thiadicarbocyanine dye.

14. The method according to claim 12, wherein the quencher is at least one selected from a group consisting of Dabcyl, TAMRA, Eclipse, DDQ, QSY, Blackberry Quencher, Black Hole Quencher, Qxl, Iowa black FQ, Iowa black RQ, and IRDye QC-1.

15. The method according to claim 8, wherein the method selectively amplifies the target nucleic acid genes by using a clamping probe complementarily binding to wild type genes, and thus inhibiting elongation of polymerase, and simultaneously detecting the existence or concentration of multiple target nucleic acids by using at least one detection probe for detecting target nucleic acids.

16. The method according to claim 8, wherein the detection probe and clamping probe bind to the same strand of the target nucleic acid chain to perform inhibition of wild type genes and detection of target nucleic acid genes simultaneously.

17. The method according to claim 8, wherein the detection probe and clamping probe bind to different strands of the target nucleic acid chain to perform inhibition of wild type genes and detection of target nucleic acid genes simultaneously.

18. The method according to claim 8, wherein the detection of target nucleic acid using a probe mixture enables simultaneous analysis of real-time amplification curve and melting curve.

19. The method according to claim 8, wherein the method comprises: (a) mixing a probe mixture comprising a clamping probe and a detection probe and a primer with a test specimen including the target nucleic acids and hybridizing the mixture to obtain a real-time amplification curve; (b) obtaining a melting curve of the detection probe from the amplification product by varying temperature after the amplification process; and (c) analyzing the real-time amplification curve and melting curve obtained separately, sequentially or simultaneously.

20. The method according to claim 19, wherein the amplification is performed through real-time polymerase chain reaction (PCR).

21. The method according to claim 19, further comprising adding 5-20 PCR cycles, in addition to the step of obtaining a real-time amplification curve, before obtaining a melting curve in (b).

22. The method according to claim 8, further comprising: (a) mixing a probe mixture comprising a clamping probe and a detection probe and a primer with a test specimen including the target nucleic acids and hybridizing the mixture to obtain a real-time amplification curve; and (b) analyzing the real-time amplification curve obtained.

23. The method according to claim 8, further comprising: (a) mixing a probe mixture comprising a clamping probe and a detection probe and a primer with a test specimen including the target nucleic acids and hybridizing the mixture; (b) melting the hybridized product by varying temperature to obtain a melting curve; and (c) analyzing the melting curve obtained.

24. A kit comprising a probe mixture according to any one of claims 1, 2 and 3 to 7.

* * * * *

SEQUENCE LISTING

```
<160> NUMBER OF SEQ ID NOS: 42

<210> SEQ ID NO 1
<211> LENGTH: 13
<212> TYPE: DNA
<213> ORGANISM: Artificial Sequence
<220> FEATURE:
<223> OTHER INFORMATION: pna probe(K12-G)

<400> SEQUENCE: 1
acgccagcag ctc                                                          13

<210> SEQ ID NO 2
<211> LENGTH: 13
<212> TYPE: DNA
<213> ORGANISM: Artificial Sequence
<220> FEATURE:
<223> OTHER INFORMATION: pna probe(K12-G-L-ala)

<400> SEQUENCE: 2
acgccagcag ctc                                                          13

<210> SEQ ID NO 3
<211> LENGTH: 13
<212> TYPE: DNA
<213> ORGANISM: Artificial Sequence
<220> FEATURE:
<223> OTHER INFORMATION: pna probe(K12-G-D-ala)

<400> SEQUENCE: 3
acgccagcag ctc                                                          13

<210> SEQ ID NO 4
<211> LENGTH: 13
<212> TYPE: DNA
<213> ORGANISM: Artificial Sequence
<220> FEATURE:
<223> OTHER INFORMATION: pna probe(K12-G-L-Glu)

<400> SEQUENCE: 4
```

```
acgccagcag ctc                                                        13

<210> SEQ ID NO 5
<211> LENGTH: 13
<212> TYPE: DNA
<213> ORGANISM: Artificial Sequence
<220> FEATURE:
<223> OTHER INFORMATION: pna probe(K12-G-D-Glu)

<400> SEQUENCE: 5
acgccagcag ctc                                                        13

<210> SEQ ID NO 6
<211> LENGTH: 13
<212> TYPE: DNA
<213> ORGANISM: Artificial Sequence
<220> FEATURE:
<223> OTHER INFORMATION: pna probe(K12-G-L-Lys)

<400> SEQUENCE: 6
acgccagcag ctc                                                        13

<210> SEQ ID NO 7
<211> LENGTH: 13
<212> TYPE: DNA
<213> ORGANISM: Artificial Sequence
<220> FEATURE:
<223> OTHER INFORMATION: pna probe(K12-G-D-Lys)

<400> SEQUENCE: 7
acgccagcag ctc                                                        13

<210> SEQ ID NO 8
<211> LENGTH: 13
<212> TYPE: DNA
<213> ORGANISM: Artificial Sequence
<220> FEATURE:
<223> OTHER INFORMATION: pna probe(K12-G-pa)

<400> SEQUENCE: 8
ctcgacgacc gca                                                        13

<210> SEQ ID NO 9
<211> LENGTH: 13
<212> TYPE: DNA
<213> ORGANISM: Artificial Sequence
<220> FEATURE:
<223> OTHER INFORMATION: pna probe(K12-G-L-ala-pa)

<400> SEQUENCE: 9
ctcgacgacc gca                                                        13

<210> SEQ ID NO 10
<211> LENGTH: 13
<212> TYPE: DNA
<213> ORGANISM: Artificial Sequence
<220> FEATURE:
<223> OTHER INFORMATION: pna probe(K12-G-D-ala-pa)

<400> SEQUENCE: 10
ctcgacgacc gca                                                        13

<210> SEQ ID NO 11
<211> LENGTH: 13
<212> TYPE: DNA
```

```
<213> ORGANISM: Artificial Sequence
<220> FEATURE:
<223> OTHER INFORMATION: pna probe(K12-G-L-Glu-pa)

<400> SEQUENCE: 11
ctcgacgacc gca                                                        13

<210> SEQ ID NO 12
<211> LENGTH: 13
<212> TYPE: DNA
<213> ORGANISM: Artificial Sequence
<220> FEATURE:
<223> OTHER INFORMATION: pna probe(K12-G-D-Glu-pa)

<400> SEQUENCE: 12
ctcgacgacc gca                                                        13

<210> SEQ ID NO 13
<211> LENGTH: 13
<212> TYPE: DNA
<213> ORGANISM: Artificial Sequence
<220> FEATURE:
<223> OTHER INFORMATION: pna probe(K12-G-L-Lys-pa)

<400> SEQUENCE: 13
ctcgacgacc gca                                                        13

<210> SEQ ID NO 14
<211> LENGTH: 13
<212> TYPE: DNA
<213> ORGANISM: Artificial Sequence
<220> FEATURE:
<223> OTHER INFORMATION: pna probe(K12-G-D-Lys-pa)

<400> SEQUENCE: 14
ctcgacgacc gca                                                        13

<210> SEQ ID NO 15
<211> LENGTH: 15
<212> TYPE: DNA
<213> ORGANISM: Artificial Sequence
<220> FEATURE:
<223> OTHER INFORMATION: pna probe(SW1116-G12A-62-AP15)

<400> SEQUENCE: 15
ggagctgctg gcgta                                                      15

<210> SEQ ID NO 16
<211> LENGTH: 13
<212> TYPE: DNA
<213> ORGANISM: Artificial Sequence
<220> FEATURE:
<223> OTHER INFORMATION: pna probe(A549-G12S-58-AP13)

<400> SEQUENCE: 16
ggagctagtg gcg                                                        13

<210> SEQ ID NO 17
<211> LENGTH: 13
<212> TYPE: DNA
<213> ORGANISM: Artificial Sequence
<220> FEATURE:
<223> OTHER INFORMATION: pna probe(xxx-G12R-61-AP13)

<400> SEQUENCE: 17
ggagctcgtg gcg                                                        13
```

<210> SEQ ID NO 18
<211> LENGTH: 13
<212> TYPE: DNA
<213> ORGANISM: Artificial Sequence
<220> FEATURE:
<223> OTHER INFORMATION: pna probe(MIAPaCa2 -G12C-58-AP13)

<400> SEQUENCE: 18
ggagcttgtg gcg                                              13

<210> SEQ ID NO 19
<211> LENGTH: 15
<212> TYPE: DNA
<213> ORGANISM: Artificial Sequence
<220> FEATURE:
<223> OTHER INFORMATION: pna probe(LoVo-G13D-61-AP15)

<400> SEQUENCE: 19
gctggtgacg taggc                                            15

<210> SEQ ID NO 20
<211> LENGTH: 13
<212> TYPE: DNA
<213> ORGANISM: Artificial Sequence
<220> FEATURE:
<223> OTHER INFORMATION: pna probe(Internal control)

<400> SEQUENCE: 20
gcggtggtcg agg                                              13

<210> SEQ ID NO 21
<211> LENGTH: 17
<212> TYPE: DNA
<213> ORGANISM: Artificial Sequence
<220> FEATURE:
<223> OTHER INFORMATION: pna probe(K12,13 CP)

<400> SEQUENCE: 21
cctacgccac cagctcc                                          17

<210> SEQ ID NO 22
<211> LENGTH: 17
<212> TYPE: DNA
<213> ORGANISM: Artificial Sequence
<220> FEATURE:
<223> OTHER INFORMATION: pna probe(K12,13 CP glu)

<400> SEQUENCE: 22
cctacgccac cagctcc                                          17

<210> SEQ ID NO 23
<211> LENGTH: 19
<212> TYPE: DNA
<213> ORGANISM: Artificial Sequence
<220> FEATURE:
<223> OTHER INFORMATION: pna probe(K12 down CP)

<400> SEQUENCE: 23
ggagctggtg gcgtaggca                                        19

<210> SEQ ID NO 24
<211> LENGTH: 27
<212> TYPE: DNA
<213> ORGANISM: Artificial Sequence
<220> FEATURE:

<223> OTHER INFORMATION: DNA oligomer(>5-up 0C)

<400> SEQUENCE: 24
gtagttggag ctgctggcgt aggcaag    27

<210> SEQ ID NO 25
<211> LENGTH: 27
<212> TYPE: DNA
<213> ORGANISM: Artificial Sequence
<220> FEATURE:
<223> OTHER INFORMATION: DNA oligomer(>1-up wild)

<400> SEQUENCE: 25
gtagttggag ctggtggcgt aggcaag    27

<210> SEQ ID NO 26
<211> LENGTH: 20
<212> TYPE: DNA
<213> ORGANISM: Artificial Sequence
<220> FEATURE:
<223> OTHER INFORMATION: Primer(BJC2005-F)

<400> SEQUENCE: 26
aaggcctgct gaaaatgact    20

<210> SEQ ID NO 27
<211> LENGTH: 22
<212> TYPE: DNA
<213> ORGANISM: Artificial Sequence
<220> FEATURE:
<223> OTHER INFORMATION: Primer(BJC2005-R)

<400> SEQUENCE: 27
ggtcctgcac cagtaatatg ca    22

<210> SEQ ID NO 28
<211> LENGTH: 18
<212> TYPE: DNA
<213> ORGANISM: Artificial Sequence
<220> FEATURE:
<223> OTHER INFORMATION: Primer(T790M-forward)

<400> SEQUENCE: 28
tccaccgtgc agctcatc    18

<210> SEQ ID NO 29
<211> LENGTH: 20
<212> TYPE: DNA
<213> ORGANISM: Artificial Sequence
<220> FEATURE:
<223> OTHER INFORMATION: Primer(T790M-reverse)

<400> SEQUENCE: 29
gtctttgtgt tcccggacat    20

<210> SEQ ID NO 30
<211> LENGTH: 14
<212> TYPE: DNA
<213> ORGANISM: Artificial Sequence
<220> FEATURE:
<223> OTHER INFORMATION: T790M-detection probe MGB-taqman

<400> SEQUENCE: 30
agctgcatga tgag    14

<210> SEQ ID NO 31

```
<211> LENGTH: 17
<212> TYPE: DNA
<213> ORGANISM: Artificial Sequence
<220> FEATURE:
<223> OTHER INFORMATION: pna probe (T790M clamping probe)

<400> SEQUENCE: 31
gctcatcacg cagctca                                                  17

<210> SEQ ID NO 32
<211> LENGTH: 13
<212> TYPE: DNA
<213> ORGANISM: Artificial Sequence
<220> FEATURE:
<223> OTHER INFORMATION: pna probe (G12D S1)

<400> SEQUENCE: 32
gagctgatgg cgt                                                      13

<210> SEQ ID NO 33
<211> LENGTH: 13
<212> TYPE: DNA
<213> ORGANISM: Artificial Sequence
<220> FEATURE:
<223> OTHER INFORMATION: pna probe (G12D S2)

<400> SEQUENCE: 33
gagctgatgg cgt                                                      13

<210> SEQ ID NO 34
<211> LENGTH: 14
<212> TYPE: DNA
<213> ORGANISM: Artificial Sequence
<220> FEATURE:
<223> OTHER INFORMATION: pna probe (G12V S1)

<400> SEQUENCE: 34
ggagctgttg gcgt                                                     14

<210> SEQ ID NO 35
<211> LENGTH: 17
<212> TYPE: DNA
<213> ORGANISM: Artificial Sequence
<220> FEATURE:
<223> OTHER INFORMATION: pna probe (K12 Clamping-1)

<400> SEQUENCE: 35
atctggtggc gtaggca                                                  17

<210> SEQ ID NO 36
<211> LENGTH: 15
<212> TYPE: DNA
<213> ORGANISM: Artificial Sequence
<220> FEATURE:
<223> OTHER INFORMATION: pna probe (K12 Clamping-2)

<400> SEQUENCE: 36
ctggtggcgt aggca                                                    15

<210> SEQ ID NO 37
<211> LENGTH: 11
<212> TYPE: DNA
<213> ORGANISM: Artificial Sequence
<220> FEATURE:
<223> OTHER INFORMATION: pna probe (G12D N2)

<400> SEQUENCE: 37
```

```
tggagctgat g                                                11

<210> SEQ ID NO 38
<211> LENGTH: 11
<212> TYPE: DNA
<213> ORGANISM: Artificial Sequence
<220> FEATURE:
<223> OTHER INFORMATION: pna probe(G12V N2)

<400> SEQUENCE: 38
tggagctgtt g                                                11

<210> SEQ ID NO 39
<211> LENGTH: 20
<212> TYPE: DNA
<213> ORGANISM: Artificial Sequence
<220> FEATURE:
<223> OTHER INFORMATION: primer(G12/13 F1)

<400> SEQUENCE: 39
aggtactggt ggagtatttg                                       20

<210> SEQ ID NO 40
<211> LENGTH: 23
<212> TYPE: DNA
<213> ORGANISM: Artificial Sequence
<220> FEATURE:
<223> OTHER INFORMATION: primer(G12/13 F2)

<400> SEQUENCE: 40
gtgacatgtt ctaatatagt cac                                   23

<210> SEQ ID NO 41
<211> LENGTH: 22
<212> TYPE: DNA
<213> ORGANISM: Artificial Sequence
<220> FEATURE:
<223> OTHER INFORMATION: primer(G12/13 RC1)

<400> SEQUENCE: 41
gttctaaatg gagataacaa cc                                    22

<210> SEQ ID NO 42
<211> LENGTH: 24
<212> TYPE: DNA
<213> ORGANISM: Artificial Sequence
<220> FEATURE:
<223> OTHER INFORMATION: primer(G12/13 RC2)

<400> SEQUENCE: 42
tagcagttcc gtgagaacgg atgc                                  24
```